(12) United States Patent  
Tomoto et al.

(10) Patent No.: US 9,262,687 B2  
(45) Date of Patent: Feb. 16, 2016

(54) IMAGE PROCESSING APPARATUS AND METHOD OF OPERATION OF IMAGE PROCESSING APPARTUS

(71) Applicant: OLYMPUS MEDICAL SYSTEMS CORP., Tokyo (JP)

(72) Inventors: Yusuke Tomoto, Tokyo (JP); Hirokazu Nishimura, Hachioji (JP); Kenichi Tanaka, Kariya (JP); Sawako Shibata, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 57 days.

(21) Appl. No.: 14/336,340

(22) Filed: Jul. 21, 2014

(65) Prior Publication Data

US 2015/0003715 A1 Jan. 1, 2015

Related U.S. Application Data

(63) Continuation of application No. PCT/JP2013/079883, filed on Nov. 5, 2013.

(30) Foreign Application Priority Data

Dec. 19, 2012 (JP) ................................ 2012-277090

(51) Int. Cl.
*G06K 9/46* (2006.01)
*G06T 7/00* (2006.01)
*G02B 23/26* (2006.01)
(Continued)

(52) U.S. Cl.
CPC .......... *G06K 9/4604* (2013.01); *A61B 1/00009* (2013.01); *A61B 1/043* (2013.01); *G02B 23/24* (2013.01); *G02B 23/26* (2013.01); *G06K 9/0014* (2013.01); *G06T 7/0012* (2013.01); *G06T 7/0083* (2013.01); *A61B 1/00045* (2013.01); *G06K 2209/053* (2013.01); *G06K 2209/40* (2013.01); *G06T 2207/10068* (2013.01); *G06T 2207/30024* (2013.01); *G06T 2207/30096* (2013.01)

(58) Field of Classification Search
None
See application file for complete search history.

(56) References Cited

U.S. PATENT DOCUMENTS

2006/0050966 A1* 3/2006 Nishimura ............ G06T 7/0012  
382/209  
2010/0111396 A1* 5/2010 Boucheron .......... G06K 9/0014  
382/133

(Continued)

FOREIGN PATENT DOCUMENTS

EP 2 520 214 A1 11/2012  
JP 2005157902 A 6/2005  
(Continued)

OTHER PUBLICATIONS

Yao, "VS Classification System," Zoom Gastroscopy, 2009, Chapter 12, pp. 107-118.

(Continued)

*Primary Examiner* — Utpal Shah  
(74) *Attorney, Agent, or Firm* — Oliff PLC

(57) ABSTRACT

An image processing apparatus includes a feature value calculating section that calculates a feature value from an image picked up of a living mucous membrane, an extraction section that extracts a structure corresponding to the feature value, and a region division section that divides the structure into partial regions according to a predetermined condition.

3 Claims, 26 Drawing Sheets

(51) Int. Cl.
  *A61B 1/00* (2006.01)
  *G06K 9/00* (2006.01)
  *G02B 23/24* (2006.01)
  *A61B 1/04* (2006.01)

(56) References Cited

U.S. PATENT DOCUMENTS

2012/0237094 A1* 9/2012 Kurihara .............. G06T 7/0085
  382/128
2012/0327205 A1 12/2012 Takahashi

FOREIGN PATENT DOCUMENTS

| JP | A-2006-141734 | 6/2006 |
| JP | 2009039515 A | 2/2009 |
| JP | A-2009-142552 | 7/2009 |
| JP | A-2011-516200 | 5/2011 |
| JP | A-2011-135983 | 7/2011 |
| JP | A-2011-167349 | 9/2011 |
| JP | 2012192125 A | 10/2012 |
| WO | WO 2011/080996 A1 | 7/2011 |

OTHER PUBLICATIONS

Aug. 26, 2014 Office Action issued in Japanese Patent Application No. 2014-531444.
Dec. 24, 2014 Office Action issued in Japanese Patent Application No. 2014-531444.
Kudoh, "Depressed type early colorectal cancer," *MB Gastro.*, 1993, vol. 3, No. 5, pp. 47-53 (with translation).
Inoue et al., "Magnifying endoscopic diagnosis of esophageal disorders," *Tokyo Medical and Dental University*, 2001, vol. 13, No. 3, pp. 301-308 (with translation).
Frangi et al., "Multiscale Vessel Enahancement Filtering," Image Sciences Institute, vol. 1496, Springer Verlag, Berlin, Germany, pp. 130-137, 1998.
Dec. 10, 2013 International Search report issued in International Application No. PCT/JP2013/079883.

* cited by examiner $f_{1A} = \sigma_{S1A} + \sigma_{S2A} \rightarrow \min$ $f_{1B} = \sigma_{S1B} + \sigma_{S2B} \rightarrow \min$ $f_{1C} = \sigma_{S1C} + \sigma_{S2C} \rightarrow \min$

FIG. 19

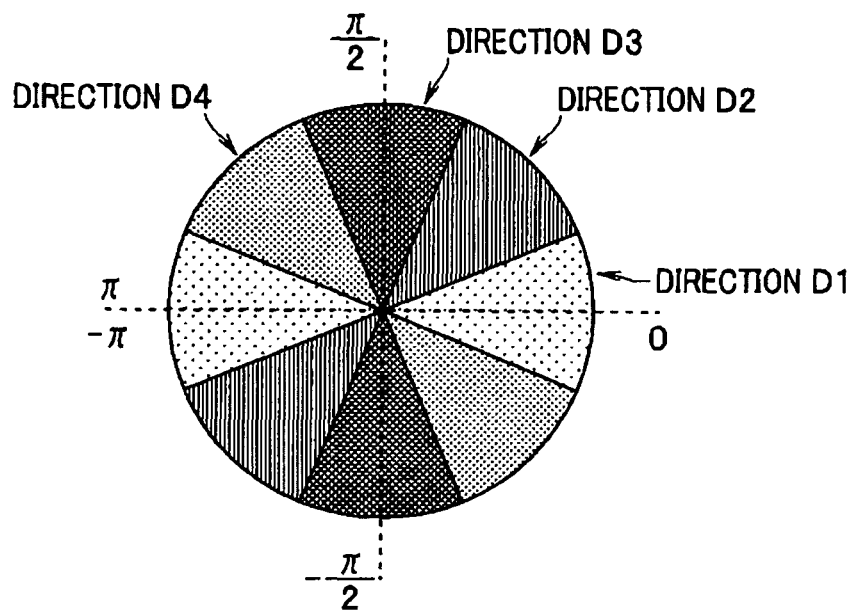

DIRECTION D1 $\left(-\frac{\pi}{8}, \frac{\pi}{8}\right], \left(\frac{7\pi}{8}, \pi\right], \left[-\pi, -\frac{7\pi}{8}\right]$ DIRECTION D2 $\left(\frac{\pi}{8}, \frac{3\pi}{8}\right], \left(-\frac{7\pi}{8}, -\frac{5\pi}{8}\right]$ DIRECTION D3 $\left(\frac{3\pi}{8}, \frac{5\pi}{8}\right], \left(-\frac{5\pi}{8}, -\frac{3\pi}{8}\right]$ DIRECTION D4 $\left(\frac{5\pi}{8}, \frac{7\pi}{8}\right], \left(-\frac{3\pi}{8}, -\frac{\pi}{8}\right]$ $(-\pi \leqq \theta < \pi)$

RUNNING DIRECTIONS
AT RESPECTIVE PIXEL POSITIONS

SG

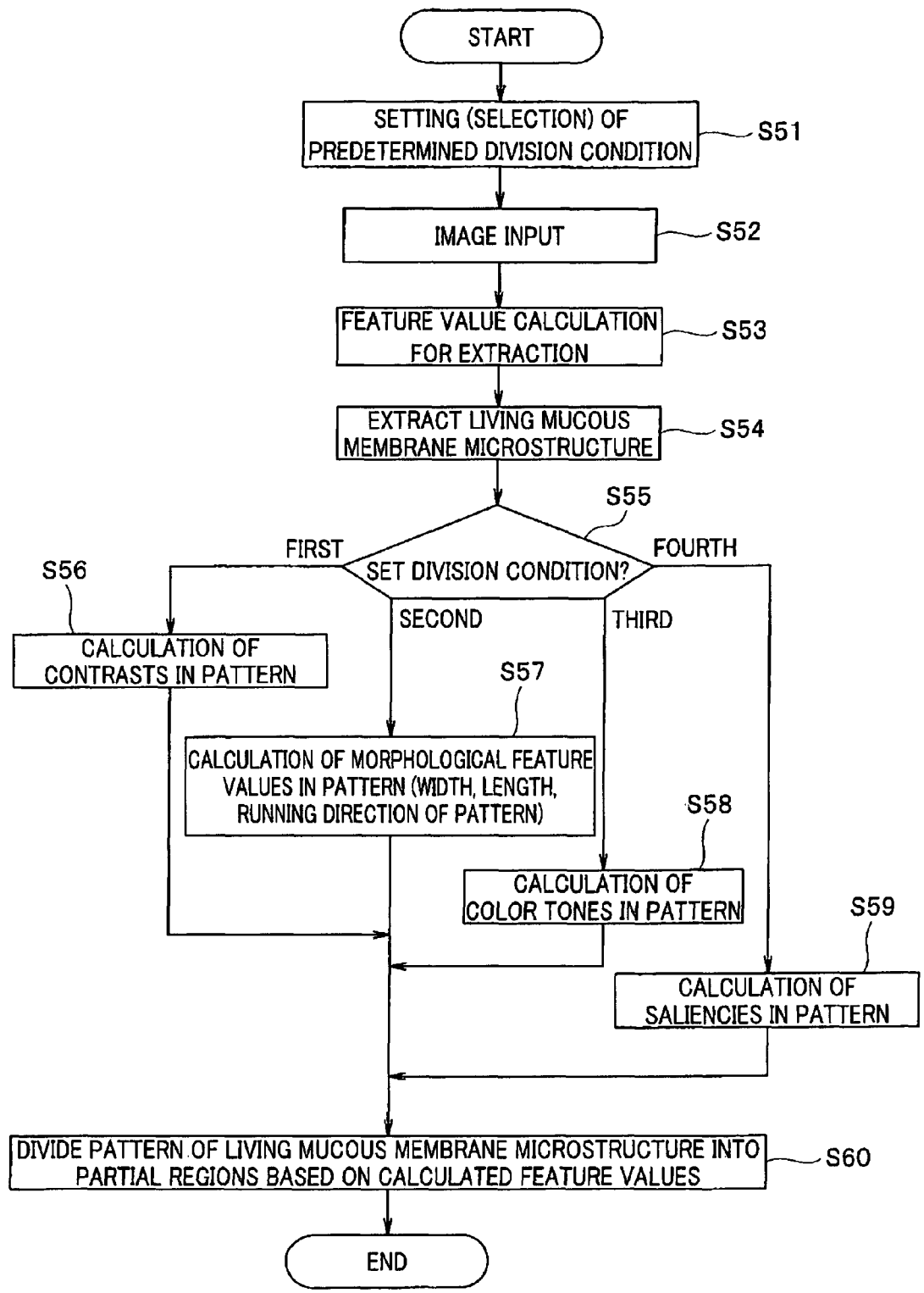

IMAGE PROCESSING APPARATUS AND METHOD OF OPERATION OF IMAGE PROCESSING APPARTUS

CROSS REFERENCE TO RELATED APPLICATION

This application is a continuation application of PCT/JP2013/079883 filed on Nov. 5, 2013 and claims benefit of Japanese Application No. 2012-277090 filed in Japan on Dec. 19, 2012, the entire contents of which are incorporated herein by this reference.

BACKGROUND OF THE INVENTION

1. Field of the Invention

The present invention relates to an image processing apparatus and a method of operation of an image processing apparatus for performing image processing of a medical image picked up of a living mucous membrane.

2. Description of the Related Art

Techniques that, based on a result of calculation of feature values in a medical image obtained by image pickup of a body tissue, divide the medical image into regions to detect a region where a predetermined target object exists have conventionally been used.

For example, Japanese Patent Application Laid-Open Publication No. 2006-141734 discloses a region division technique that, based on image signals resulting from pickup of an image of an object, extracts a living mucous membrane microstructure using binarization processing, performs labelling processing of the binarized image generated by setting pixel values of pixels corresponding to the living mucous membrane microstructure to 1 and pixels other than the pixels to 0, identifying components included in the living mucous membrane microstructure, and allocates regions to the respective components of the living mucous membrane microstructure based on structure information on the respective components.

Also, Japanese Patent Application Laid-Open Publication No. 2011-516200 discloses a technique that automatically traces one or more paths of one or more blood vessels in a retina image, automatically identifies blood vessel segments included in the traced blood vessels, and uses the blood vessel segments to calculate feature values of the blood vessels.

Also, in recent years, with the increase in resolution of endoscope (which may be capsule endoscope) systems, the popularization of magnifying endoscopes and the popularization of narrow-band light observation, observation of living mucous membrane microstructures such as microscopic blood vessel images and pit structures has been growing in importance.

Information on the forms and distribution of living mucous membrane microstructures in a body tissue is useful for discrimination between normal tissues and tumor tissues, and further for diagnosis of a lesion such as estimation of a penetration depth of a cancer. For these living mucous membrane microstructure findings, diagnostics based on various classifications for various organs and diseases is proposed and used. For example, large intestine pit pattern observation (see, for example, "Early-Stage Depressed Large Intestine Cancer", Eishin Kudo, Monthly Book Gastro, Kabushikigaisha Zen-nihon Byo-in Shuppan-kai, May 15, 1993, third volume, fifth issue, p.p. 47-54), MV Pattern, which is a microscopic blood vessel finding in a mucous membrane of a stomach, and MS Pattern, which is a mucous membrane surface microscopic structure (epithelial structure) finding (see, for example, "Zoom Gastroscopy" (2009), Kenshi Yao and Toshiyuki Matsui) and IPCL, which is a microscopic blood vessel finding in a mucous membrane in an esophagus (see, for example, "magnifying endoscopic diagnosis of esophageal diseases", Haruhiro Inoue and five others, Gastroenterological Endoscopy, Kabushiki Kaisha Tokyo Igakusha, Mar. 25, 2001, 13-th issue, third issue, p.p. 301-308) are known. Also, blood vessel findings in bronchi are drawing attention although there is no clear category for such blood vessel findings.

However, since such diagnoses are based mainly on the experience and knowledge of the respective doctors, as a technique for eliminating differences in experience and knowledge, for example, there is a demand for providing a differential diagnosis support technique for living mucous membrane microstructure findings using an image analysis technique. Such differential diagnosis support technique is being studied as one of computer-aided diagnoses (CAD).

For example, in a diagnosis using an MV pattern and an MS pattern of a stomach, shape uniformity, arrangement regularity and distribution symmetry in each pattern (figure) can be important findings. These findings can be identified not directly from an image one can see, but, for example, with some kind of interpretation added thereto, such as estimating and analyzing a three-dimensional histological structure of a living mucous membrane from a visible endoscopic image.

Through such process of adding some kind of interpretation, a finding that is a target of identification may vary in such a manner that the finding is sometimes an entire pattern and sometimes only a partial pattern in an image.

In analysis of a living mucous membrane microstructure in an endoscopic image, it is essential not to simply analyze a continuous pattern one can see, but analyze a pattern corresponding to a finding by adding some kind of interpretation to the pattern.

SUMMARY OF THE INVENTION

An image processing apparatus according to an aspect of the present invention includes: an image input device that receives an input of an image obtained by image pickup of a living mucous membrane having a three-dimensional structure; an extraction device that extracts pixels corresponding to the structure appearing as a continuous pattern in the image from pixels included in the image inputted to the image input device; a feature value calculating device that calculates a feature value representing a feature of the structure extracted by the extraction device; and a region division device that extracts, based on the feature value calculated by the feature value calculating device, pixels corresponding to a structure that is continuous in a three-dimensional space, from the pixels corresponding to the structure.

A method of operation of an image processing apparatus according to an aspect of the present invention includes: an image inputting step of inputting an image obtained by image pickup of a living mucous membrane having a three-dimensional structure to an image processing apparatus; an extraction step of extracting, via the image processing apparatus, pixels corresponding to the structure appearing as a continuous pattern in the image from pixels included in the image inputted in the image input step; a feature value calculating step of calculating, via the image processing apparatus, a feature value representing a feature of the structure extracted by the extraction step; and a region division step of extracting, via the image processing apparatus, pixels corresponding to a structure that is continuous in a three-dimensional space, from the pixels corresponding to the structure, based on the feature value calculated in the feature value calculating step.

BRIEF DESCRIPTION OF THE DRAWINGS

FIG. 19 is a schematic diagram illustrating an example in which a running direction of a living mucous membrane microstructure is quantified;

FIG. 29 is a flowchart illustrating an example of processing for calculation of feature values according to a division condition and division into regions based on a result of the calculation in the third embodiment.

DETAILED DESCRIPTION OF THE PREFERRED EMBODIMENTS

Embodiments of the present invention will be described below with reference to the drawings.

(First Embodiment)

Figure 1:
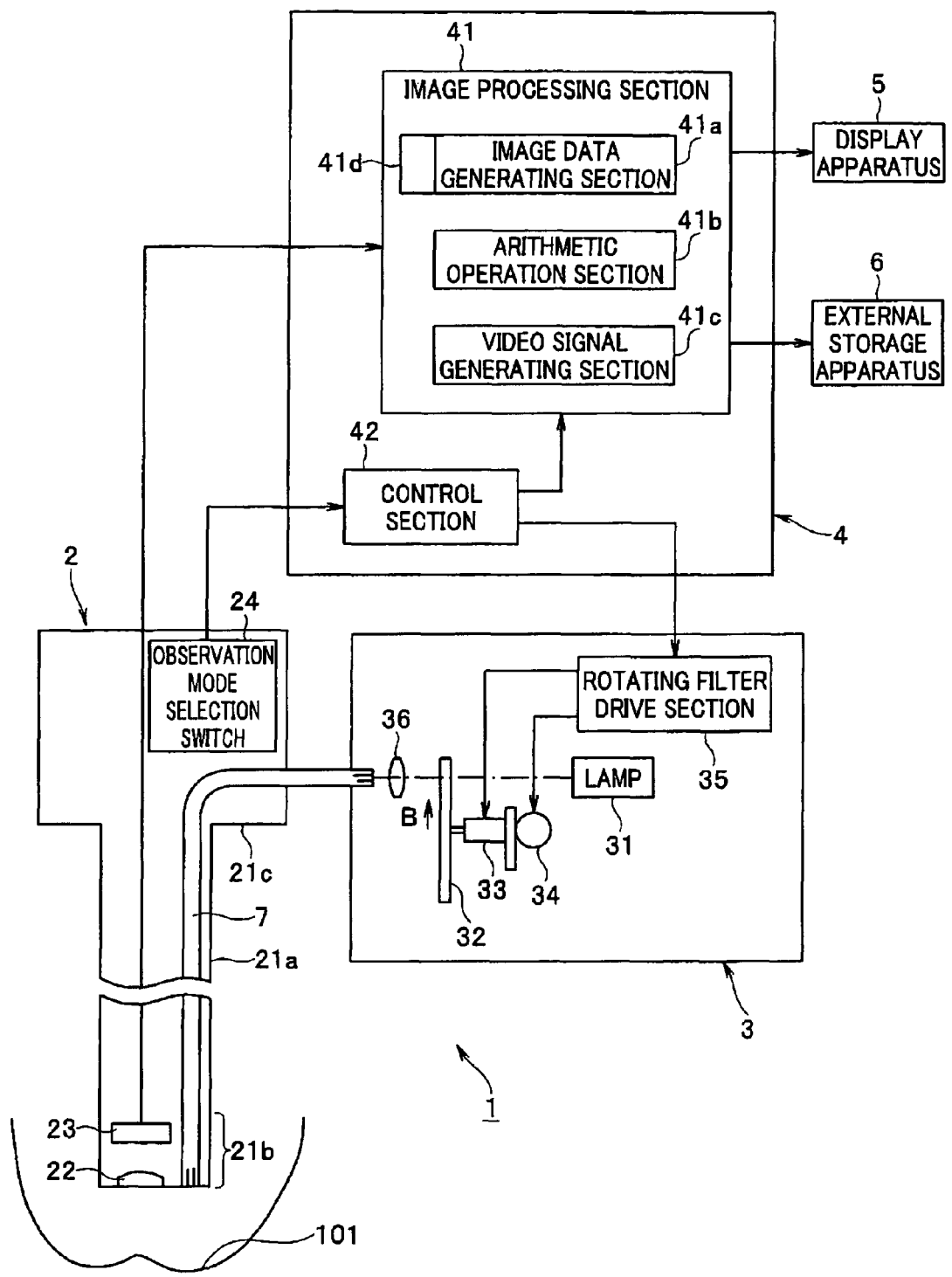
FIG. 1 is a diagram illustrating a configuration of a main part of an endoscope apparatus including a medical image processing apparatus according to a first embodiment.

As illustrated in FIG. 1, an endoscope apparatus 1 includes an endoscope 2 to be inserted into a body cavity of a subject, the endoscope 2 outputting an image obtained by image pickup of an object such as a body tissue 101 in the body cavity in the form of a signal, a light source apparatus 3 that emits illuminating light for illuminating the body tissue 101, a processor 4 that provides a medical image processing apparatus that performs various processing on the output signal from the endoscope 2, a display apparatus 5 that displays an image according to the resulting video signal from the processor 4, and an external storage apparatus 6 that stores the output signal according to a result of the processing in the processor 4.

The endoscope 2 includes an insertion portion 21a having an elongated shape and dimensions that enable the insertion portion 21a to be inserted into a body cavity of a subject, a distal end portion 21b provided on the distal end side of the insertion portion 21a, and an operation portion 21c provided on the proximal end side of the insertion portion 21a. Also, inside the insertion portion 21a, a light guide 7 that conveys the illuminating light emitted by the light source apparatus 3 to the distal end portion 21b is inserted.

An end face (light entrance end face) of the light guide 7 is detachably connected to the light source apparatus 3. Also, the other end face (light exit end face) of the light guide 7 is disposed in the vicinity of a non-illustrated illumination optical system provided at the distal end portion 21b of the endoscope 2. With such configuration, illuminating light emitted by the light source apparatus 3 exits toward the body tissue 101 in the body cavity through the light guide 7 connected to the light source apparatus 3 and the non-illustrated illumination optical system provided at the distal end portion 21b.

In the distal end portion 21b of the endoscope 2, an objective optical system 22 that forms an optical image of an object, and a charge-coupled device (abbreviated as CCD) 23 disposed at a position where an image from the objective optical system 22 is formed, the charge-coupled device 23 providing an image pickup section that picks up and thereby obtains an optical image as an image, are provided. Also, in the operation portion 21c of the endoscope 2, an observation mode selection switch 24 that allows provision of an instruction for switching an observation mode to a normal light observation mode or a narrow-band light observation mode is provided.

The light source apparatus 3 includes a white light source 31 including, e.g., a xenon lamp, a rotating filter 32 that converts white light emitted from the white light source 31 into frame-sequential illuminating light, a motor 33 that drives the rotating filter 32 to rotate, a motor 34 that moves the rotating filter 32 and the motor 33 in a direction perpendicular to a light exit optical path of the white light source 31 (symbol B in FIG. 1), a rotating filter drive section 35 that drives the motors 33 and 34 based on control performed by a control section 42 in the processor 4, and a light collection optical system 36 that collects the illuminating light passed through the rotating filter 32 and supplies the illuminating light to the light entrance end face of the light guide 7.

Figure 2:
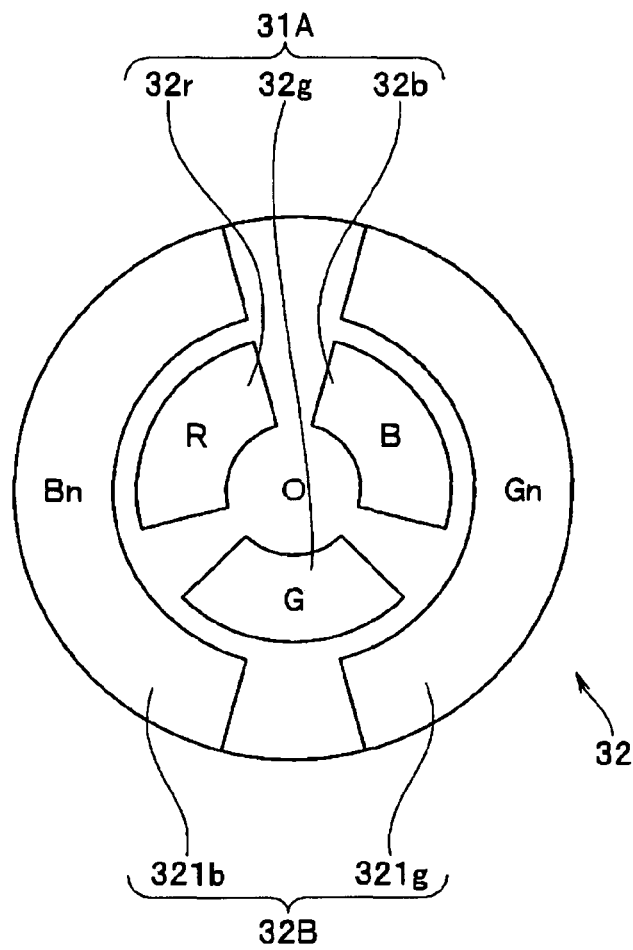
FIG. 2 is a diagram illustrating an example of a configuration of a rotating filter included in a light source apparatus in FIG. 1.

As illustrated in FIG. 2, the rotating filter 32 have a disc shape with a rotating shaft in a center thereof, and includes a first filter group 32A including a plurality of filters provided along a circumferential direction of the inner peripheral side and a second filter group 32B including a plurality of filters provided along a circumferential direction of the outer peripheral side. Upon transmission of a driving force of the motor 33 to the rotating shaft, the rotating filter 32 rotates. Note that a part of the rotating filter 32 other than parts where the respective filters in the first filter group 32A and the second filter group 32B are disposed includes a light-blocking member.

The first filter group 32A includes a R filter 32r that transmits light in a red wavelength band, a G filter 32g that transmits light in a green wavelength band and a B filter 32b that transmits light in a blue wavelength band, each of which is circumferentially provided on the inner peripheral side of the rotating filter 32.

Figure 3:
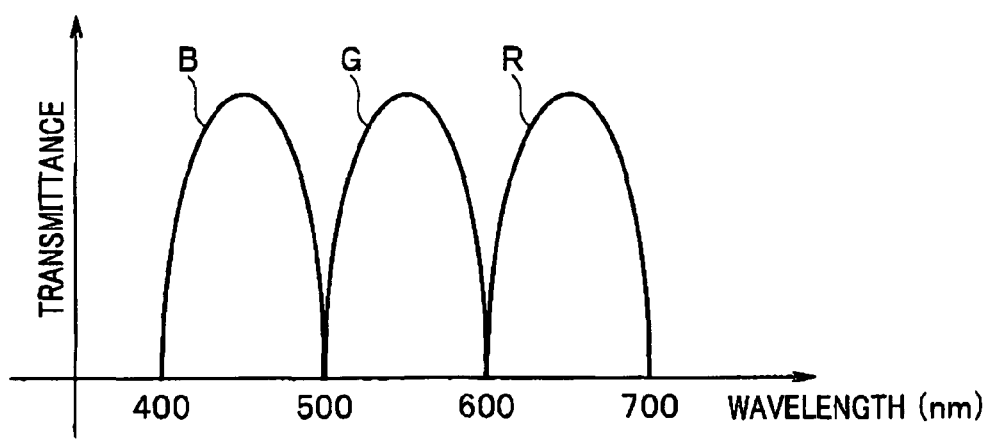
FIG. 3 is a diagram illustrating an example of a transmission characteristic of each filter included in a first filter group in FIG. 2.

The R filter 32r, for example, as illustrated in FIG. 3, has a configuration that mainly transmits light from 600 to 700 nm (R light). Also, the G filter 32g, for example, as illustrated in FIG. 3, has a configuration that allows transmission of mainly light from 500 to 600 nm (G light). Furthermore, the B filter 32b, for example, as illustrated in FIG. 3, has a configuration that allows transmission of mainly light from 400 to 500 nm (B light). Here, in FIG. 3, the R filter 32r, the G filter 32g and the B filter 32b are simply indicated as R, G and B.

White light emitted by the white light source 31 passes through the first filter group 32A, whereby wide-band light for the normal light observation mode is produced.

The second filter group 32B includes a Bn filter 321b that allows transmission of blue and narrow-band light and a Gn filter 321g that allows transmission of green and narrow-band light, each of which is circumferentially provided on the outer peripheral side of the rotating filter 32.

Figure 4:
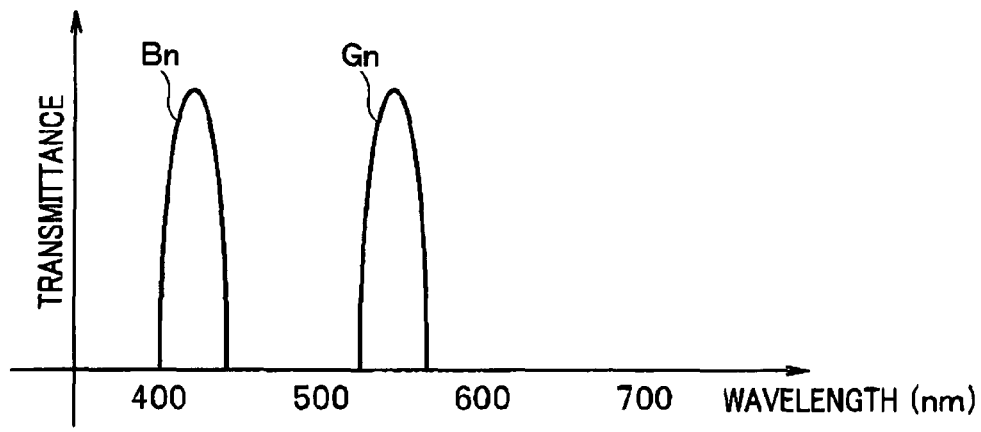
FIG. 4 is a diagram illustrating an example of a transmission characteristic of each filter included in a second filter group in FIG. 2.

The Bn filter 321b, for example, as illustrated in FIG. 4, is set to have a central wavelength of around 415 nm and is configured to transmit light in a narrow band (Bn light) compared to B light.

Also, the Gn filter 321g, for example, as illustrated in FIG. 4, has a central wavelength of around 540 nm and is configured to transmit light in a narrow band (Gn light) compared to G light. Here, in FIG. 4, the Bn filter 321b and the Gn filter 321g are simply indicated by Bn and Gn.

As a result of the white light emitted by the white light source 31 passing through the second filter group 32B, discretized narrow-band light in a plurality of bands for the narrow-band light observation mode is generated.

The processor 4 has a configuration having a function as a medical image processing apparatus of the present embodiment.

More specifically, as illustrated in FIG. 1, the processor 4 includes an image processing section 41 and a control section 42. Also, the image processing section 41 includes an image data generating section 41a, an arithmetic operation section 41b, a video signal generating section 41c, and an image input section 41d that receives an input of a medical image picked up by the CCD 23 included in the image pickup section of the endoscope 2.

The image data generating section 41a in the image processing section 41 subjects an output signal from the endoscope 2 to processing such as denoising and A/D conversion based on the control performed by the control section 42 and thereby generates image data corresponding to the image obtained by the CCD 23.

Note that around an input section of the image data generating section 41a, an image input section 41d that receives the input of the medical image (the output signal from the endoscope 2) picked up by the CCD 23 included in the image pickup section is provided. Although a medical image is inputted to the image data generating section 41a via the image input section 41d, a configuration in which the image data generating section 41a includes the image input section 41d may be employed.

The arithmetic operation section 41b in the image processing section 41 performs predetermined processing using the image data generated by the image data generating section 41a and thereby extracts a living mucous membrane microstructure in an epithelium of a mucous membrane (abbreviated as epithelial structure) from the image data obtained by pickup of the image of the body tissue 101 and further divides the living mucous membrane microstructure into partial regions according to a predetermined division condition.

Here, in the present embodiment, it is assumed that a continuous living mucous membrane microstructure pattern is included in the image data and furthermore, region division processing for distinguish between a living mucous membrane microstructure corresponding to an important finding for diagnosis and regions other than that in the living mucous membrane microstructure.

Figure 16A:
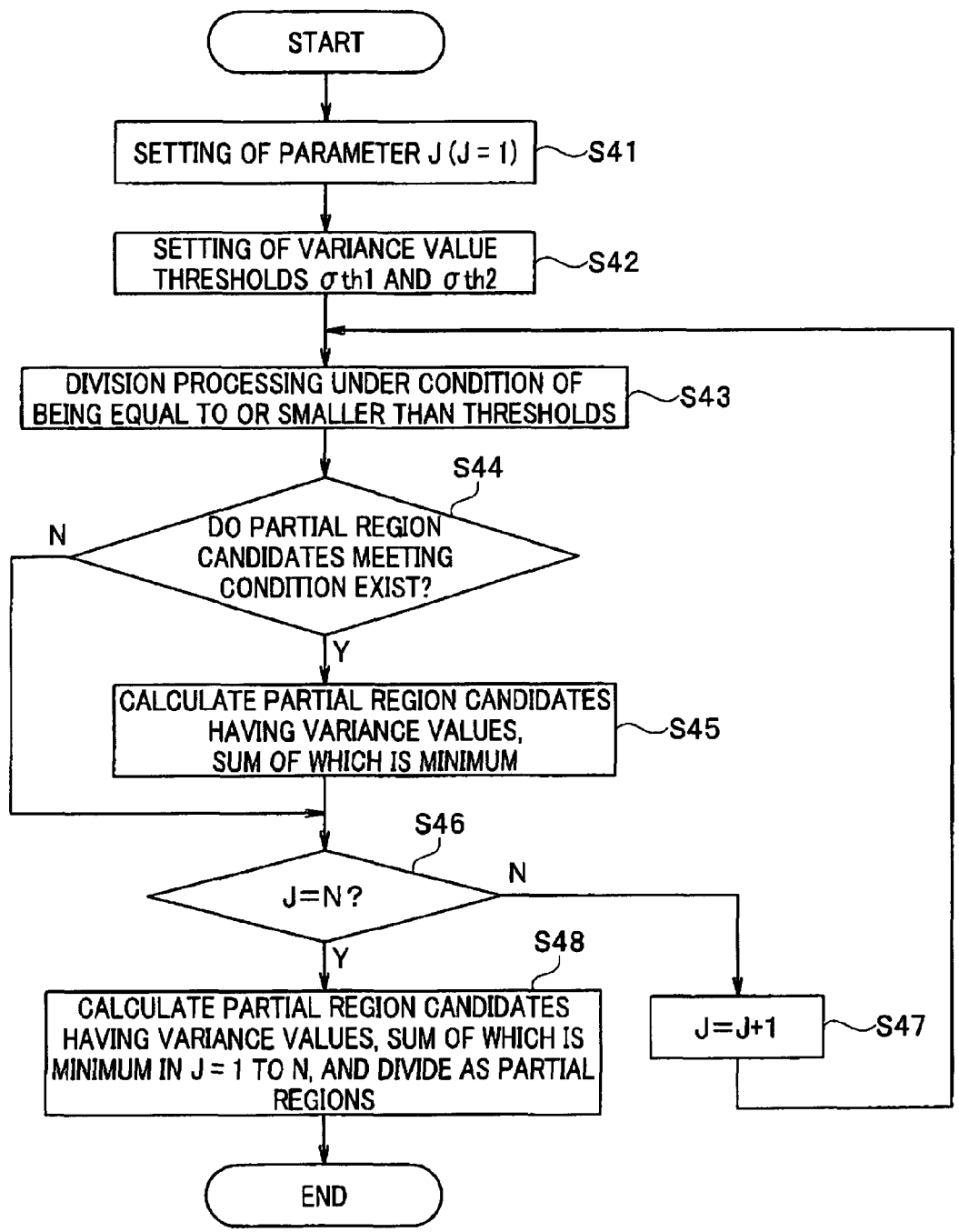
FIG. 16A is a flowchart illustrating processing for division into partial regions under the condition that the sum of variance values is minimum.
Figure 16B:
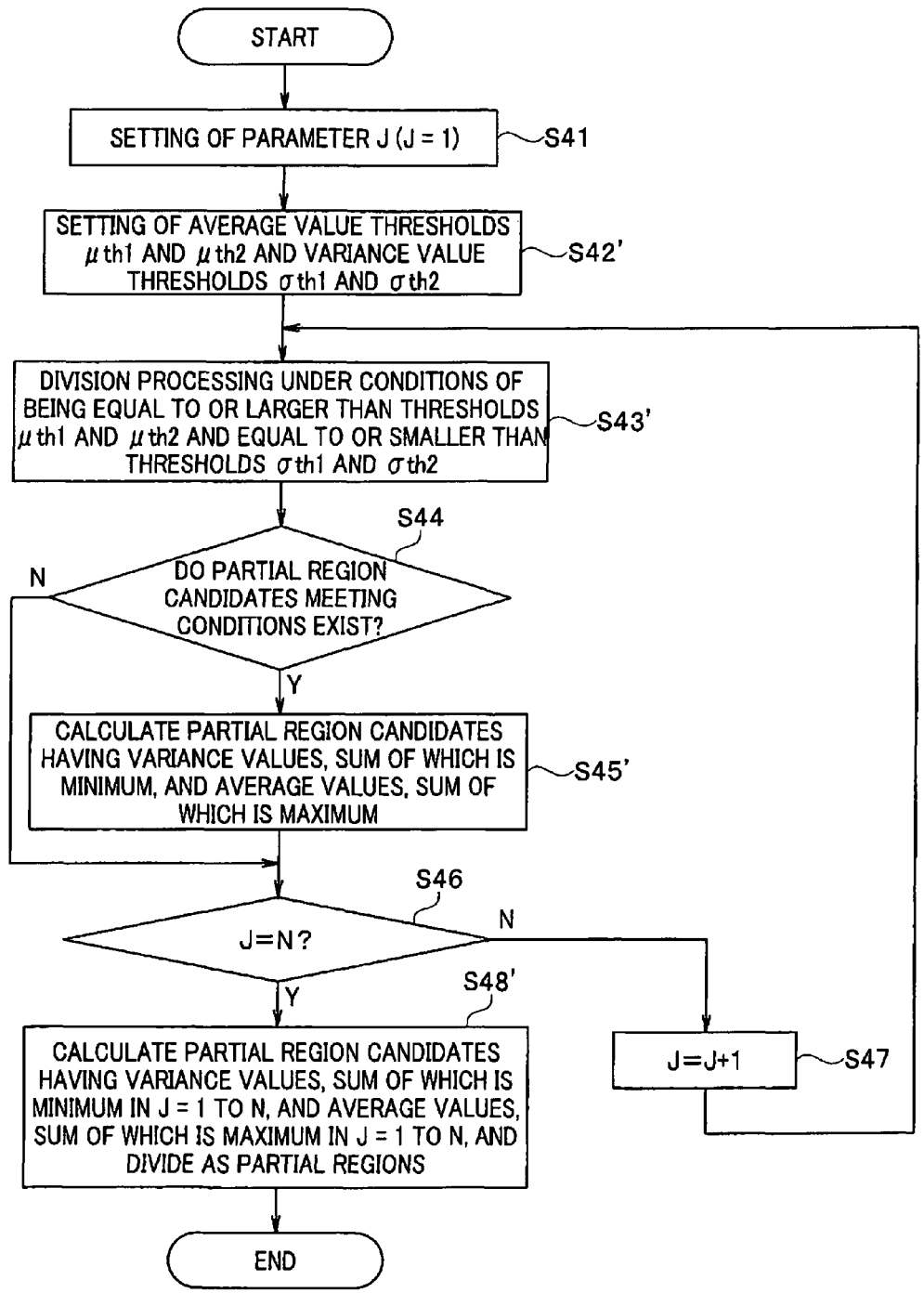
FIG. 16B is a flowchart illustrating process for division into partial regions under the condition that the sum of average values is maximum and the sum of variance values is minimum.
Figure 16C:
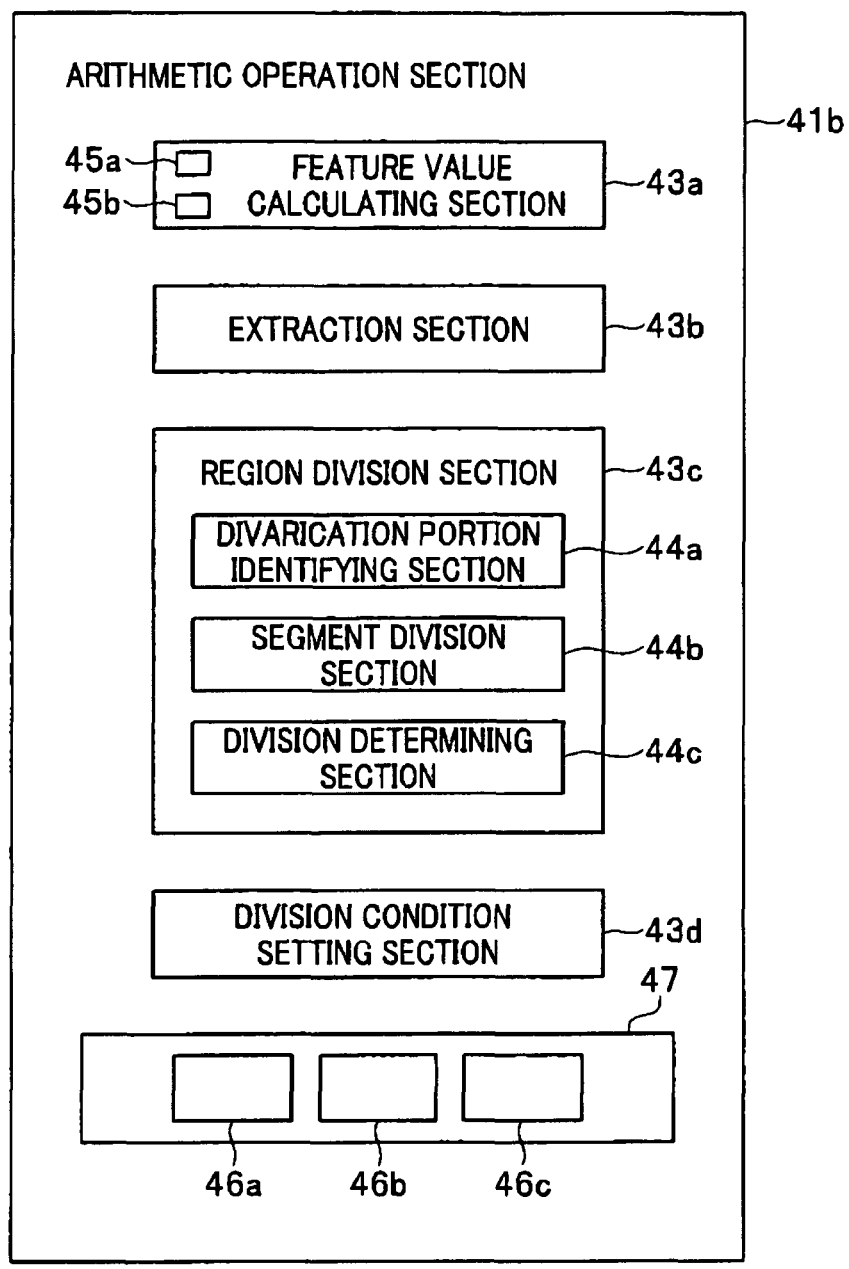
FIG. 16C is a block diagram illustrating a main configuration of an arithmetic operation section in a second embodiment of the present invention.

Also, a method for such region division processing is installed as a program in a non-illustrated ROM or a memory 47 illustrated in FIG. 16C, and a CPU included in the arithmetic operation section 41b performs the region division processing according to the program.

The video signal generating section 41c in the image processing section 41 subjects the image data generated by the image data generating section 41a to processing such as gamma conversion and D/A conversion and thereby generates a video signal, and outputs the video signal to, e.g., the display apparatus 5.

If the control section 42 detects that an instruction to switch the observation mode to the normal light observation mode is provided, based on an instruction from the observation mode selection switch 24, the control section 42 controls the rotating filter drive section 35 to emit wide-band light for the normal light observation mode from the light source apparatus 3. Then, the rotating filter drive section 35, based on the control performed by the control section 42, makes the motor 34 operate so as to insert the first filter group 32A on the emission optical path of the white light source 31 and retract the second filter group 32B from the emission optical path of the white light source 31.

Also, if the control section 42 detects that an instruction to switch the observation mode to the narrow-band light observation mode is provided, based on an instruction from the observation mode selection switch 24, the control section 42 controls the rotating filter drive section 35 to emit narrow-band light of the plurality of bands for the narrow-band light observation mode from the light source apparatus 3.

Then, the rotating filter drive section 35, based on the control performed by the control section 42, makes the motor 34 operate so as to insert the second filter group 32B on the emission optical path of the white light source 31 and retract the first filter group 32A from the emission optical path of the white light source 31.

With the configuration of the endoscope apparatus 1 described above, if the normal light observation mode is selected, an image having colors substantially similar to those of the case where an observation target object such as the body tissue 101 is viewed by the naked eye (normal light image) is displayed on the display apparatus 5 and furthermore is stored in the external storage apparatus 6. Also, with the configuration of the endoscope apparatus 1 described above, if the narrow-band light observation mode is selected, an image with blood vessels included in the body tissue 101 enhanced (narrow-band light image) is displayed on the display apparatus 5 and furthermore is stored in the external storage apparatus 6.

Figure 5:
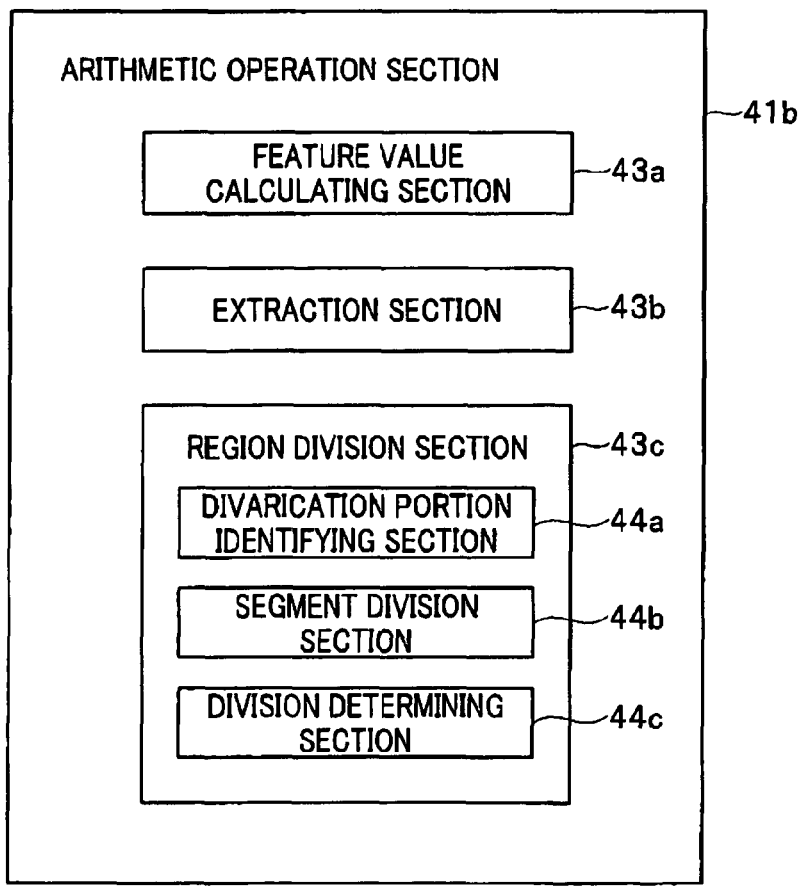
FIG. 5 is a block diagram illustrating a main configuration of an arithmetic operation section in FIG. 1.

As illustrated in FIG. 5, the arithmetic operation section 41b (included in the medical image processing apparatus) includes a feature value calculating section 43a that provides feature value calculating means for calculating at least one feature value from a medical image inputted to the above-described image input section 41d, an extraction section 43b that provides extraction means for extracting (an image part of) a living mucous membrane microstructure appearing as a continuous pattern (figure) in the medical image based on the feature value calculated by the feature value calculating section 43a, and a region division section 43c that provides region dividing means for dividing the living mucous membrane microstructure extracted by the extraction section 43b into partial regions according to a predetermined division condition based on the feature value calculated by the feature value calculating section 43a.

Also, the region division section 43c includes a divarication portion identifying section 44a that serves as divarication portion identifying means for identifying a divarication portion from the living mucous membrane microstructure extracted from the extraction section 43b, and a segment division section 44b that detects or generates living mucous membrane microstructure segments resulting from the living mucous membrane microstructure being divided by each divarication portion identified by the divarication portion identifying section 44a.

Also, the region division section 43c includes a division determining section (or a division deciding section) 44c that determines or decides whether or not to divide the living mucous membrane microstructure segments generated by the segment division section 44b into partial regions according to a predetermined division condition set by a division condition setting section 43d based on feature values calculated for the respective living mucous membrane microstructure segments.

The division determining section 44c determines or decides, based on the feature values calculated for the respective living mucous membrane microstructure segments, whether or not to divide the respective living mucous membrane microstructure segments into partial regions based on whether or not the respective living mucous membrane microstructure segments meet the predetermined division condition set by the division condition setting section 43d or correspond to the predetermined division condition. Here, the present invention is not limited to the configuration illustrated in FIG. 5 in which the arithmetic operation section 41b has functions of, e.g., the feature value calculating section 43a, the extraction section 43b and the region division section 43c, and each of the feature value calculating section 43a, the extraction section 43b and the region division section 43c may be separate from the arithmetic operation section 41b or may be formed by dedicated hardware.

The image processing section 41 included in the medical image processing apparatus having the above-described configuration includes: the image input section 41d (illustrated in FIG. 1), which serves as image input means for receiving an input of a medical image obtained by image pickup of a living mucous membrane; the feature value calculating section 43a illustrated in FIG. 5, which serves as feature value calculating means for calculating at least one feature value from the medical image inputted to the image input means; the extraction section 43b, which serves as extraction means for extracting a living mucous membrane microstructure appearing as a continuous pattern from the medical image based on the feature value calculated by the feature value calculating means; and the region division section 43c, which serves as region division means for dividing the living mucous membrane microstructure extracted by the extraction means into partial regions according to a predetermined division condition, based on the feature value calculated by the feature value calculating means.

Figure 6:
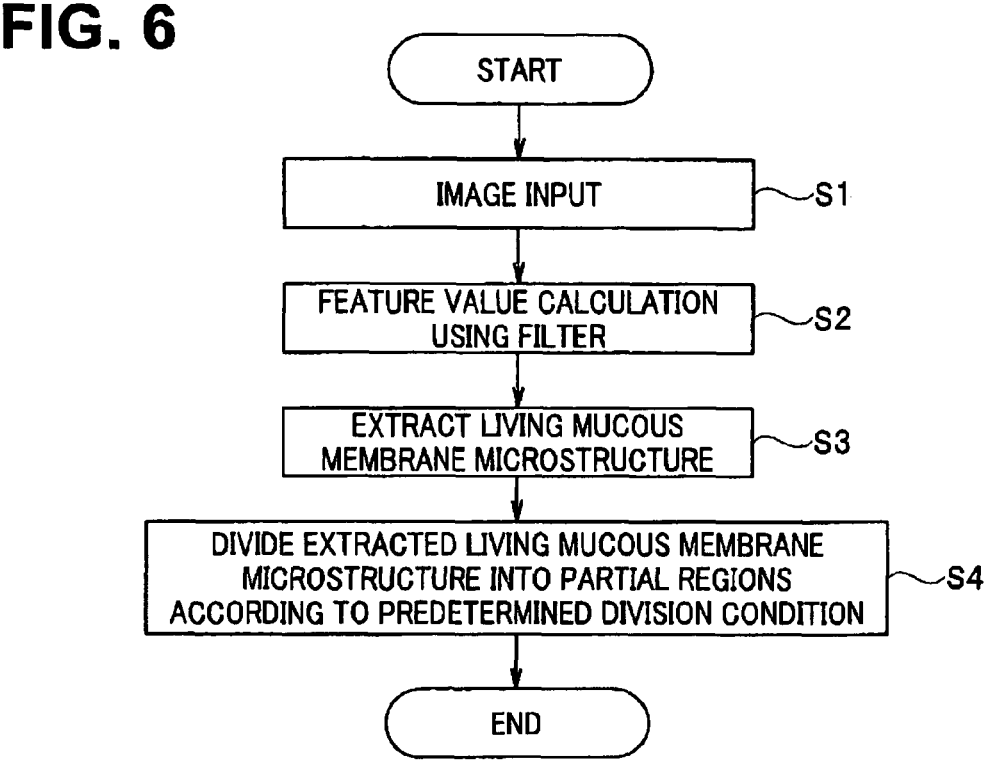
FIG. 6 is a flowchart illustrating an example of processing performed in an image processing section in the first embodiment of the present invention.

Also, as illustrated in FIG. 6, a medical image processing method according to the present embodiment executes: step S1, which serves as an image input step of inputting a medical image obtained by image pickup of a living mucous membrane; step S2, which serves as a feature value calculating step of calculating at least one feature value from the medical image inputted in the image input step (using, e.g., a filter); step S3, which serves as an extraction step of extracting a living mucous membrane microstructure appearing as a continuous pattern in the medical image based on the feature value calculated by the feature value calculating step; and step S4, which serves as a region division step of dividing the living mucous membrane microstructure extracted by the extraction step into partial regions according to a predetermined division condition, based on the feature value calculated by the feature value calculating step.

Next, an operation (action) of the endoscope apparatus 1 including the medical image processing apparatus according to the present embodiment will be described.

First, a surgeon powers on the respective sections of the endoscope apparatus 1 and then selects the normal light observation mode via the observation mode selection switch 24. Then, the surgeon inserts the endoscope 2 into a body cavity while viewing an image displayed on the display apparatus 5 when the normal light observation mode is selected, that is, an image of colors substantially similar to those of a case where a target object is viewed by the naked eye, thereby bringing the distal end portion 21b close to a site where an observation target body tissue 101 exists.

Upon selection of the normal light observation mode via the observation mode selection switch 24, light of respective colors, i.e., R light, G light and B light are sequentially emitted from the light source apparatus 3 to the body tissue 101, and in the endoscope 2, a respective image corresponding to the light of each color is obtained.

The image data generating section 41a in the image processing section 41 receives an input of the image corresponding to the R light, the image corresponding to the G light and the image corresponding to the B light via the image input section 41d as indicated in step S1 in FIG. 6. The image data generating section 41a generates respective image data of a color component corresponding to each image.

Note that in the present embodiment, image data generated by the image data generating section 41a includes three planes of R, G and B, has an image size of a horizontal direction ISX (for example, 640 pixels) and a vertical direction ISY (for example, 480 pixels), and includes pixels each having a tone of 8 bits, i.e., 0 to 255. Also, the below description will be provided assuming that pixel values of j-th ($1 \leq j < ISX \times ISY$) pixels in the respective R, G and B planes are rj, gj and bj, respectively.

The (feature value calculating section 43a in the) arithmetic operation section 41b of the image processing section 41 may, as necessary, perform inverse gamma correction and/or noise suppression processing as non-illustrated pre-processing, based on the image data generated by the image data generating section 41a.

As indicated in step S2 in FIG. 6, (the feature value calculating section 43a of) the arithmetic operation section 41b in the image processing section 41 calculates a predetermined feature value to be used for subsequent processing, for each pixel of the image data, based on the image data generated by the image data generating section 41a.

More specifically, since a living mucous membrane microstructure has, for example, a thin linear structure, the arithmetic operation section 41b in the present embodiment uses response values from a filter that enhances (or extracts) a linear structure, as the aforementioned predetermined feature values. Note that, here, "enhance[ment]" refers to processing whereby a local region around a position of pixel for which a filter is used is outputted with a large value if the local region has a shape close to a linear structure and is outputted with a small value if the local region does not has such shape.

For the filter that enhances a linear structure, a method in which an evaluation value representing a linear structure closeness based on an eigenvalue obtained by calculation of an eigenvalue of a Hessian matrix is calculated is used. Such method is disclosed in "Multiscale Vessel Enhancement Filtering", Alejandro F. Frangi, Wiro J. Nissen, Koen L. Vincken and Max A. Viergever, LNCS, vol. 1496, Springer Verlag, Berlin, Germany, p.p. 130-137. In the present embodiment, an evaluation value is calculated for each pixel having the pixel value gj in the j-th pixel (each of all the first to (ISX× ISY)-th pixels) in the G plane in image data generated where the narrow-band light observation mode is selected.

Subsequently, as indicated in step S3, (the extraction section 43b of) the arithmetic operation section 41b in the image processing section 41 performs processing for extracting a region where a living mucous membrane microstructure exists in the body tissue 101, using the predetermined feature values calculated in step S2 in FIG. 6.

In the present embodiment, a response value from the filter that enhances a linear structure is calculated for each pixel, and a pixel whose response value is larger than a threshold T of 50 is extracted as a part of a living mucous membrane microstructure. Depending on the content of the design of the filter or the kind of the living mucous membrane microstructure to be extracted, a pixel whose response value is smaller than a threshold T' of −50 may be extracted as a part of a living mucous membrane microstructure.

The above difference in extraction occurs due to a difference in kind of the living mucous membrane microstructure: for example, blood vessels have an image density value smaller than those of the surrounding mucous membrane, and living mucous membrane microstructures such as MCE and pit patterns using pyoktanin dying, which are described in "Zoom Gastroscopy" (2009) by Kenshi Yao and Toshiyuki Matsui, tend to have an image density value larger than that of the surrounding mucous membrane.

Figure 7:
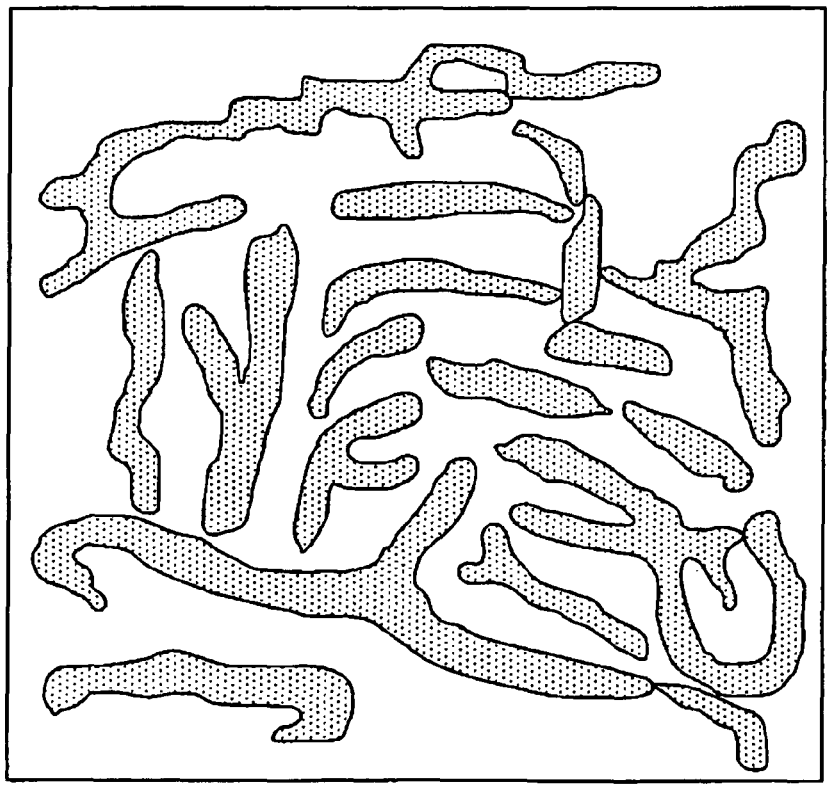
FIG. 7 is a schematic diagram illustrating an example of image data to be processed.

Note that for easy of description, the below description will be provided assuming that processing is performed for schematic image data, such as illustrated in FIG. 7, in which a region corresponding to an inner portion of each living mucous membrane microstructure (inside of each living mucous membrane microstructure) is dotted, regions corresponding to a background mucous membrane (outside of the living mucous membrane microstructures) is displayed in blank and boundaries between these two types of regions are indicated by thin solid lines.

Note that FIG. 7 schematically illustrates living mucous membrane microstructures in a gastric pyloric gland mucous membrane observed using a magnifying endoscope in the narrow-band light observation mode. Actual endoscopic images are not limited to those having image data including only living mucous membrane microstructures and background mucous membrane regions, but may be those having image data further including, for example, various kinds of structures, such as microscopic blood vessels, collecting venules and/or pits.

Even if living mucous membrane microstructures are structures that are not continuous with each other, the living mucous membrane microstructures may be imaged in a continuous pattern in an image because of three-dimensional arrangement in a depth direction of the living mucous membranes. In such case, living mucous membrane microstructures extracted in step S3 in FIG. 6 may also be extracted as a continuous pattern.

Figure 8:
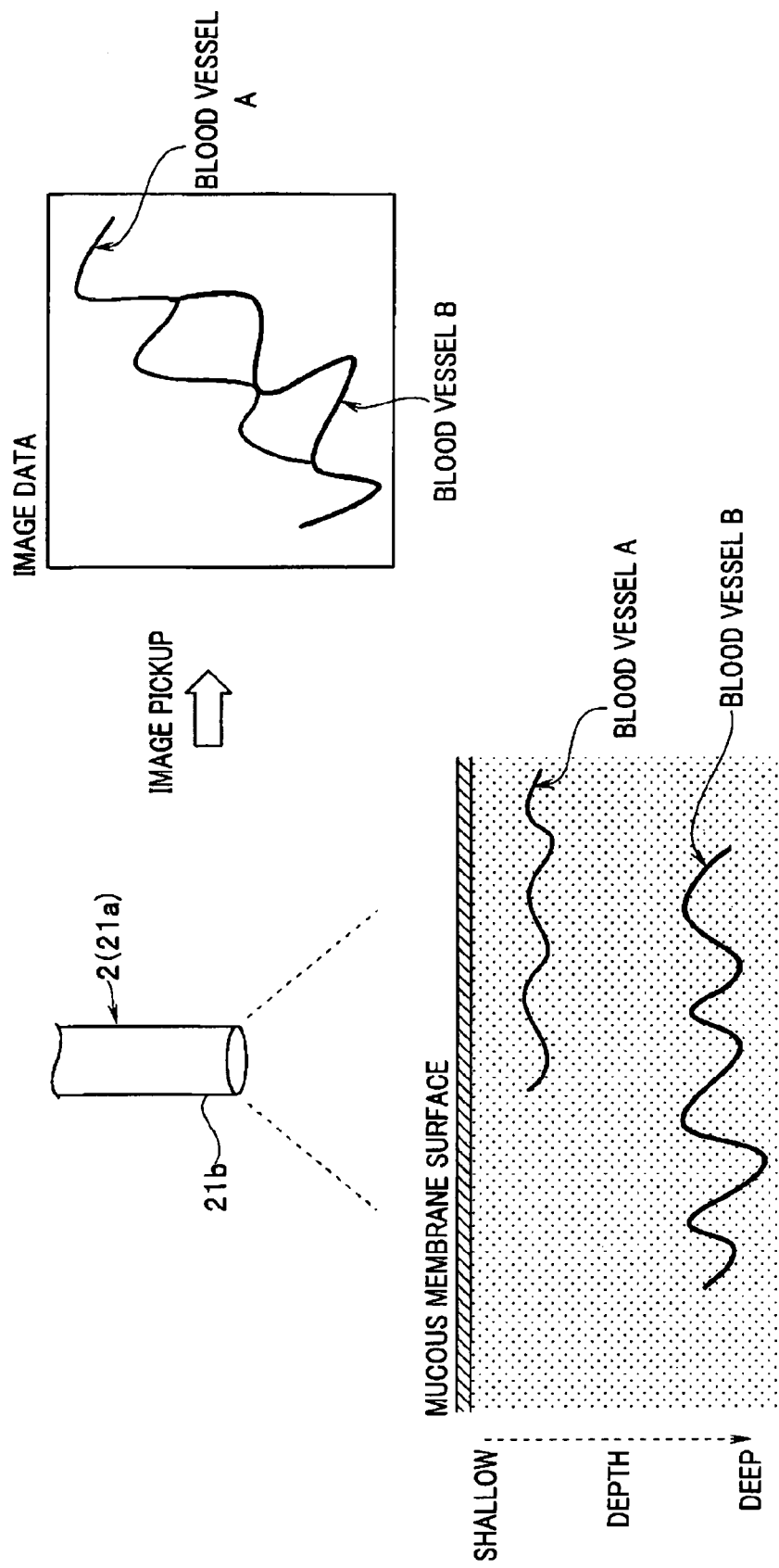
FIG. 8 is a schematic diagram illustrating an example of an image picked up of blood vessels existing in a mucous membrane and running at respective positions that are different in depth from a surface of the mucous membrane.

FIG. 8 illustrates image data obtained when an image of blood vessels running in a mucous membrane is picked up, in such case as above. As illustrated in FIG. 8, an image of a mucous membrane of a body tissue 101 is picked up by (the image pickup section provided in) the distal end portion 21b of the insertion portion 21a in the endoscope 2. Inside the mucous membrane, a thin blood vessel A runs around a shallow position from the mucous membrane surface and a thick blood vessel B runs around a position that is deeper than the blood vessel A. Image data obtained by picking up an image of a living mucous membrane in a depth direction (deepness direction) from a direction perpendicular to the mucous membrane surface, as illustrated in FIG. 8, may appear as including a continuous pattern of blood vessels in which the blood vessel A and the blood vessel B are connected.

In reality, as illustrated in FIG. 8, the blood vessel A and the blood vessel B are different from each other in position in the depth direction and thus not connected in three dimensions, it is desired to divide image data in which the blood vessel A and the blood vessel B are connected in two dimensions into partial regions corresponding to findings (in other words, corresponding to actual three-dimensional structures) (for example, the blood vessel A and the blood vessel B in FIG. 8). In the present embodiment, an image processing apparatus and an image processing method for dividing a pattern of living mucous membrane microstructures extracted in such a manner that the living mucous membrane microstructures appear as being connected in two dimensions, into partial regions corresponding to findings (for example, the blood vessel A and the blood vessel B in FIG. 8) will be described.

As described above, even if microstructures are imaged in such a manner that the microstructures superficially appear as a continuous pattern, e.g., the degree of light scattering differs depending on the respective mucous membrane cells and the degree of light absorption also differs depending on the respective blood vessels because of the difference in depth inside the mucous membrane. Such differences in scattering and absorption may cause slight differences in contrast and/or color tone in the image.

In general, it is known that while where light is projected to a semitransparent substance like a mucous membrane, red light having long wavelengths diffuses deeply over a large area, blue light having short wavelengths diffuses shallowly over a small area, and because of the effect of such light propagation characteristics, blood vessels existing in the deep side tend to be imaged with a blurred contour and a low contrast, and blood vessels in a superficial layer tend to be imaged with a sharp contour and a high contrast.

Also, in the narrow-band light observation mode, as illustrated in FIG. 4, the wavelength characteristics of projected light are those of narrow-bands, and thus, the image is largely susceptible to the effect of the aforementioned difference in light propagation characteristic due to the depths. Thus, in an image picked up in the narrow-band light observation mode, strong Bn light absorption and week Gn light absorption and scattering occur in a mucous membrane including a blood vessel in a superficial layer, and Bn light reflection and scattering and strong Gn light absorption occur in a mucous membrane including a blood vessel on the deep side.

As a result, blood vessels are imaged in such a manner that the blood vessels have different color tones depending on the depths in which the respective blood vessels exist. Furthermore, for example, in the case of blood vessels, there is the tendency that thick blood vessels run on the deep part of a mucous membrane and thin blood vessels run in the superficial layer, and thus, the blood vessels may be distinguished from one another according to the differences in thickness in the image.

If regions having different contrasts exist inside the living mucous membrane microstructure extracted in step S3 in FIG. 6, as indicated in step S4, (the region division section 43c of) the arithmetic operation section 41b in the image processing section 41 performs region division processing for dividing the living mucous membrane microstructure to partial regions according to a predetermined division condition (which is a first condition that the contrasts exhibit discontinuity or inhomogeneity (or non-identity)), based on the predetermined division condition. This predetermined division condition provides a condition suitable for, where living mucous membrane microstructures that are not continuous with each other in three dimensions appears as forming a continuous pattern in two dimensional image data resulting from picking up an image of the living mucous membrane microstructures, dividing (or extracting) the image data of the living mucous membrane microstructures into partial regions along a boundary between the discontinuous living mucous membrane microstructures (in other words, suitable for dividing or extracting image data of the living mucous membrane microstructures corresponding to findings).

In the below, definitions and conceptual description on the aforementioned "contrast(s)" and "condition for respective partial regions to exhibit continuity or homogeneity" will be provided, and then, the description of the region division processing in the present embodiment will be continued.

Figure 9:
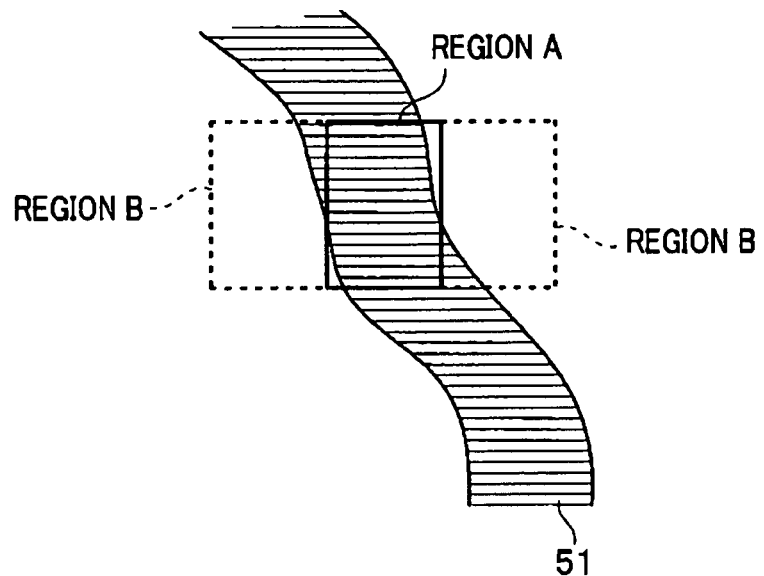
FIG. 9 is a schematic diagram illustrating an example of a definition of contrasts in a living mucous membrane microstructure.

Here, "contrast" means, for example, as illustrated in FIG. 9, a difference between an average value $\mu_A$ of image density values in an image corresponding to G light in a region A, which is a local region inside the region of a living mucous membrane microstructure 51 and an average value $\mu_B$ of image density values in an image corresponding to G light in a region B, which is a local region outside the region of the living mucous membrane microstructure 51. Then, if there is a difference in contrast (average values of the image density values) or the contrasts are different from each other, it is determined that the contrasts exhibit discontinuity or inhomogeneity and region division processing is performed.

For example, if a difference in contrast between the region A and the region B is equal to or larger than a threshold $\Delta$, it is determined that the contrasts are discontinuous or inhomogeneous and it is possible to perform processing for dividing the regions A and B into partial regions along each boundary exhibiting the contrast difference. On the other hand, if a difference in contrast is smaller than the threshold $\Delta$, it is determined that the contrasts are continuous or homogeneous and it is possible to prevent the regions A and B from being divided into partial regions at each boundary exhibiting a contrast difference that is smaller than the threshold $\Delta$. Note that contrasts exhibiting discontinuity or inhomogeneity may be abbreviated as contrasts exhibiting discontinuity.

Figure 10:
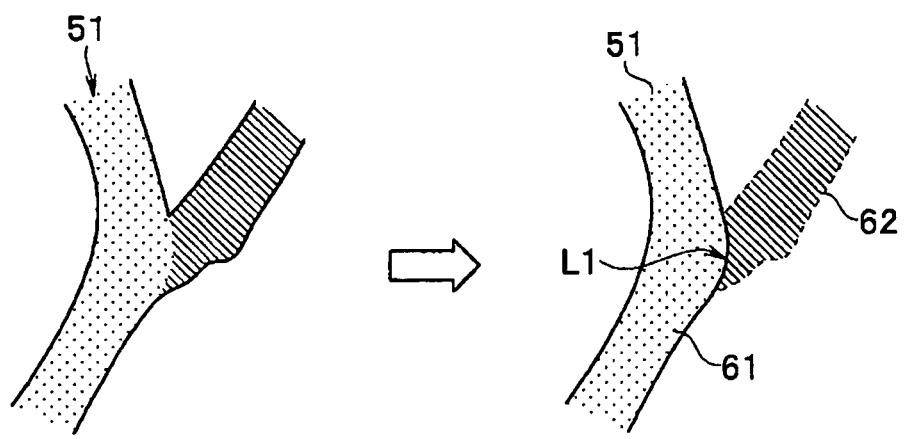
FIG. 10 is a schematic diagram illustrating example division in which region division is performed based on a contrast difference.

Also, inside the region of the living mucous membrane microstructure 51, as illustrated in the left side of FIG. 10, if there is a boundary exhibiting a contrast difference or the contrasts are different from each other, the relevant region is divided into partial regions 61 and 62 along a division line L as illustrated in the right side of FIG. 10.

Figure 11:
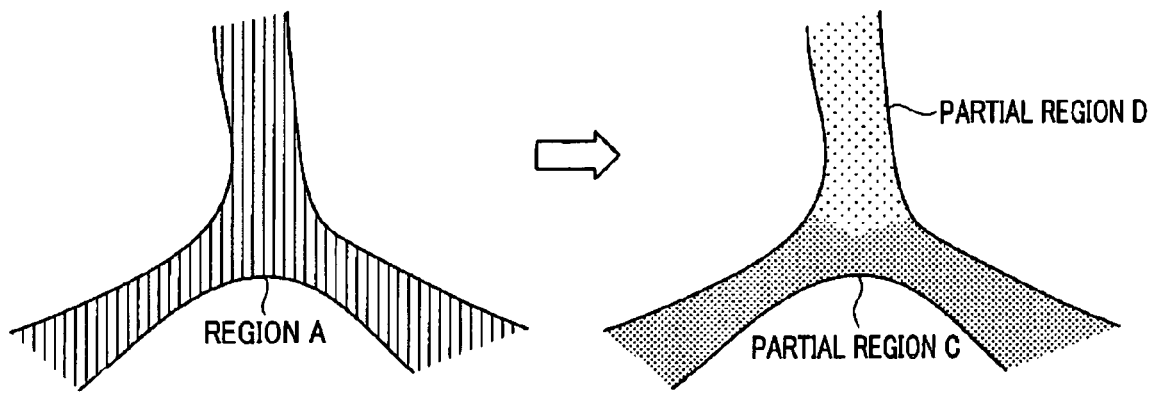
FIG. 11 is a schematic diagram illustrating a living mucous membrane microstructure and an example of a result of region division of the living mucous membrane microstructure.

Also, for a condition that respective partial regions exhibit continuity or homogeneity may be, for example, as illustrated in FIG. 11, a condition that where a region A is divided into two partial regions (a partial region C and a partial region D), variation inside each of the partial region C and the partial region D resulting from the division is smallest may be a predetermined division condition.

If the above content is expressed in another way, it is equivalent to solve an optimization problem to obtain a region division result that variation (change) in contrast of pixels belonging to the partial region C is smallest and change in contrast of pixels belonging to the partial region D is smallest. In the present embodiment, variance is used as a parameter representing a magnitude of change.

More specifically, for example, when it is intended to divide the region A illustrated in the left side of FIG. 11 into two partial regions (the partial region C and the partial region D) as illustrated in the right side of FIG. 11, where $\sigma_C$ is a variance value in contrast of the partial region C (from an average value) and $\sigma_D$ is a variance value in contrast of the partial region D (from an average value), the partial region C and the partial region D may be obtained so as to minimize the below objective function $f_1$.

$$f_1 = \sigma_C + \sigma_D \to \min \quad (1)$$

Also, the condition may be a condition that variation between the respective partial regions C and D is largest.

In another way of expression, it is equivalent to solve an optimization problem to obtain a region division result that a difference between a statistical nature in contrast of respective pixels belonging to the partial region C and a statistical nature in contrast of respective pixels belonging to the partial region D is largest. In the present embodiment, for the statistical nature, an average value is used.

More specifically, for example, as illustrated in FIG. 11, when it is intended to divide the region A into two partial regions (the partial region C and the partial region D), where $\mu_C$ is an average value of contrasts inside the partial region C and $\mu_D$ is an average value of contrasts inside the partial region D, the partial region C and the partial region D may be obtained so as to maximize the below objective function $f_2$.

$$f_2 = \mu_C + \mu_D \to \max \quad (2)$$

Furthermore, this condition may be a condition that variation inside each of the partial region C and the partial region D is smallest and variation between the respective partial regions C and D is largest.

For example, as illustrated in FIG. 11, if it is intended to divide the region A into two partial regions (the partial region C and the partial region D), where $\sigma_C$ is an variance value in contrast inside the partial region C, $\mu_C$ is an average value in contrast inside the partial region C, $\sigma_D$ is a variance value in contrast inside the partial region D and $\mu_D$ is an average value in contrast inside the partial region D, the partial region C and the partial region D may be obtained so as to maximize the below objective function $f_3$.

$$f_3 = (\mu_C + \mu_D)/(\sigma_C + \sigma_D) \to \max \quad (3)$$

The above is the conceptual description of contrast(s) and condition for respective partial regions to exhibit continuity or homogeneity, and a more specific processing flow of region division (step S4 in FIG. 6) in the present embodiment will be described below with reference to FIG. 12.

Figure 12:
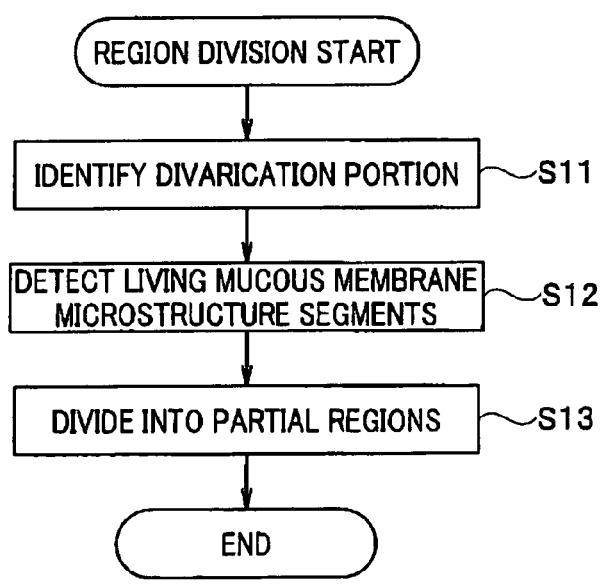
FIG. 12 is a flowchart illustrating specific example of processing in processing for division into partial regions.

As indicated in step S11 in FIG. 12, (the region division section 43c of) the arithmetic operation section 41b in the image processing section 41 identifies a divarication portion from a living mucous membrane microstructure detected by the extraction section 43b.

Figure 13A:
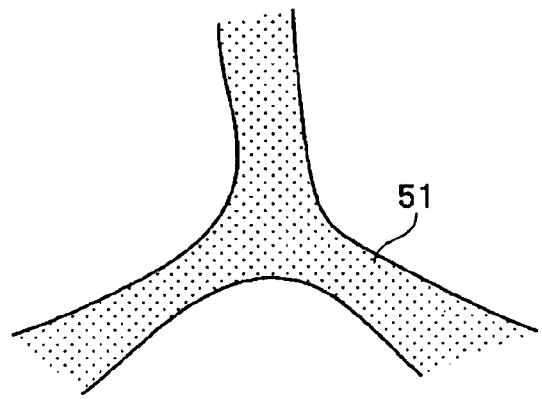
FIG. 13A is an explanatory diagram illustrating specific example of processing in processing for division into living mucous membrane microstructure segments.
Figure 13B:
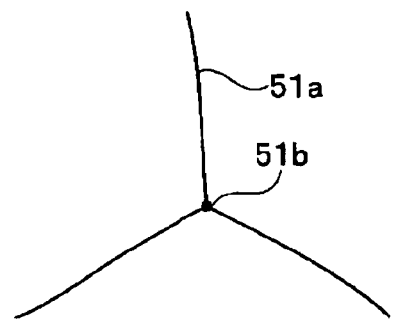
FIG. 13B is an explanatory diagram illustrating specific example of processing in processing for division into living mucous membrane microstructure segments.
Figure 13C:
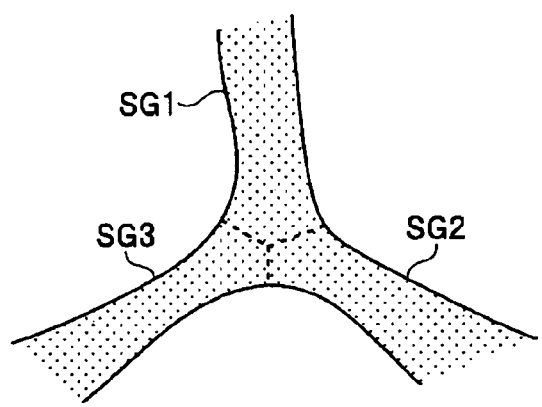
FIG. 13C is an explanatory diagram illustrating specific example of processing in processing for division into living mucous membrane microstructure segments.

Thus, the divarication portion identifying section 44a in the region division section 43c binarizes the extracted living mucous membrane microstructure and subjects the resulting living mucous membrane microstructure to thinning processing for center line detection, and identifies a pixel that is in contact with three or more pixels from among eight pixels adjacent to the pixel in the respective pixels in the image subjected to the thinning processing (referred to as "thinned image") as a (divarication point of) divarication portion. FIGS. 13A to 13C indicate specific diagrams illustrating the content of the processing by the divarication portion identifying section 44a.

A case where the extraction section 43b in the arithmetic operation section 41b extracts, for example, (an image) of a living mucous membrane microstructure 51 that divaricates in three directions such as illustrated in FIG. 13A will be described. The divarication portion identifying section 44a in the region division section 43c binarizes (the image of) the living mucous membrane microstructure 51 in FIG. 13A extracted by the extraction section 43b and subjects the image to thinning processing for center line detection to generate a thinned image 51a illustrated in FIG. 13B.

Also, the divarication portion identifying section 44a identifies a pixel that is in contact with three or more pixels from among eight pixels adjacent to the pixel in the respective pixels of the thinned image 51a as a (divarication point of a) divarication portion 51b.

The segment division section 44b in the arithmetic operation section 41b, as indicated in step S12, detects living mucous membrane microstructure segments resulting from the thinned image 51a illustrated in FIG. 13B being divided by the divarication portion 51b.

More specifically, the segment division section 44b in the arithmetic operation section 41b removes the respective divarication points from the thinned image 51a to detect thinned segments, and subjects the thinned segments to expansion processing using, for example, 7×7-size structure elements to detect three living mucous membrane microstructure segments SG1, SG2 and SG3 as illustrated by the dotted lines in FIG. 13C.

Figure 14:
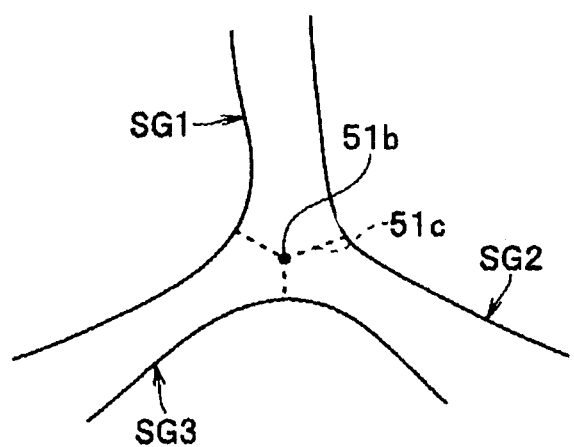
FIG. 14 is an explanatory diagram illustrating specific example of processing in processing for division into mucous membrane microstructure segments by means of processing that is different from that of the processing described with reference to FIGS. 13A to 13C.

As described with reference to FIGS. 13A to 13C, the living mucous membrane microstructure segment detection method is not limited to a method in which respective divarication points are removed from a thinned image to detect thinned segments and the thinned segments are subjected to processing for expansion in a width direction to detect living mucous membrane microstructure segments, and, as illustrated in FIG. 14, living mucous membrane microstructure segments SG1, SG2 and SG3 may be generated by dividing a living mucous membrane microstructure 51 by division lines 51c each connecting the detected divarication portions 51b and a boundary of the living mucous membrane microstructure 51. Here, each of the division lines 51c is set so that a distance between the divarication portion 51b and the relevant boundary of the living mucous membrane microstructure 51 is a minimal value.

Furthermore, as indicated in step S13, the region division section 41c in the arithmetic operation section 41b calculates feature values for each of the living mucous membrane microstructure segments SG1, SG2 and SG3 illustrated in FIG. 13C (by means of the feature value calculating section 43a), and based on the calculated feature values, divides the living mucous membrane microstructure segments SG1, SG2 and SG3 into partial regions so that the condition that contrasts in each of the partial regions resulting from the division exhibit continuity or homogeneity is met.

Note that in the present embodiment, the feature value calculated in step S2 in FIG. 6 (response value of the filter that enhances a linear structure) depends on the contrast and the magnitude of the response value is determined by the contrast, and thus, the feature value can be used as a parameter representing a contrast.

Also, the flow of specific processing by the region division section 43c in the arithmetic operation section 41b where a living mucous membrane microstructure is divided into, for example, two partial regions will be described with reference to FIGS. 15A to 15D. The segment division section 44b in the arithmetic operation section 41b generates two arbitrary living mucous membrane microstructure segment combinations from all of the living mucous membrane microstructure segments detected in step S12 in FIG. 12 and determines each of the combinations as a partial region candidate.

Figure 15A:
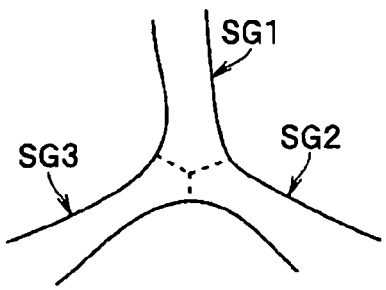
FIG. 15A is a schematic diagram for describing an example combination of living mucous membrane microstructure segments before division into regions.

FIG. 15A corresponds to a case where the three living mucous membrane microstructure segments SG1, SG2 and SG3 illustrated in FIG. 13C are partial region candidates. FIG. 15A illustrates a case where a living mucous membrane microstructure segment before division forms a trifurcated pattern. Then, as described below, the segment division section 44b divides the living mucous membrane microstructure into segments, which are partial region candidates so that one end is a divarication portion and the other end side is an end portion (although not illustrated). Also, if the other end side is a divarication portion, the living mucous membrane microstructure segment is divided in a manner similar to the above.

Figure 15B:
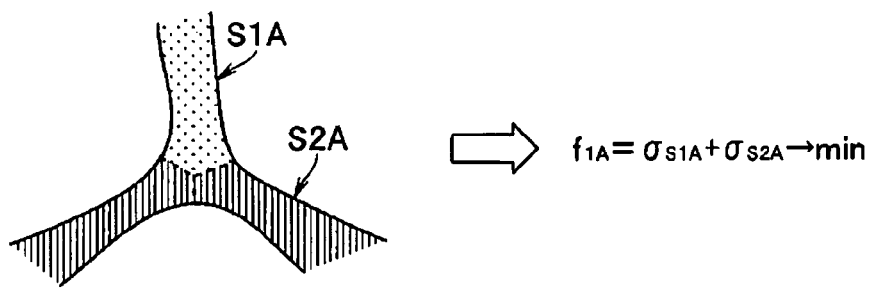
FIG. 15B is a schematic diagram for describing an example combination of living mucous membrane microstructure segments before division into regions.
Figure 15C:
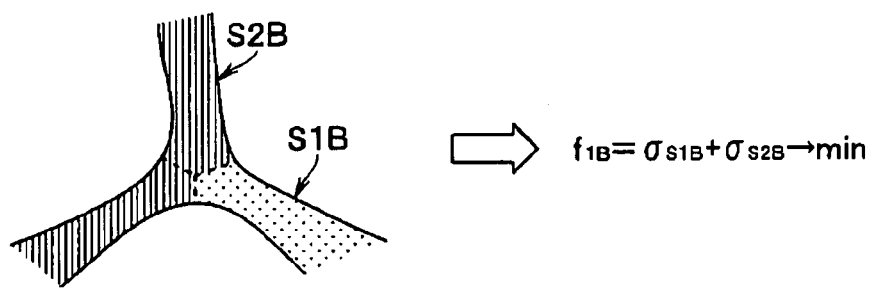
FIG. 15C is a schematic diagram for describing an example combination of living mucous membrane microstructure segments before division into regions.
Figure 15D:
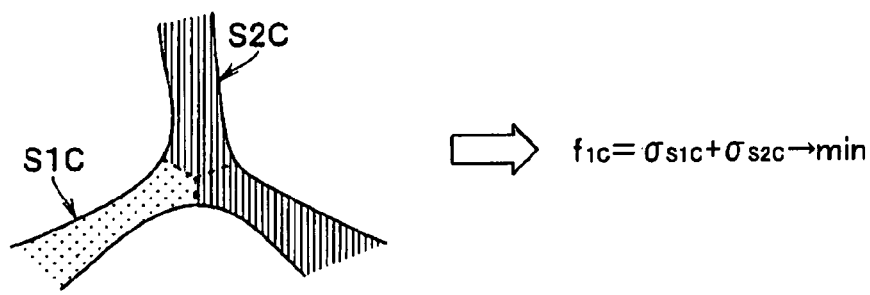
FIG. 15D is a schematic diagram for describing an example combination of living mucous membrane microstructure segments before division into regions.

More specifically, three partial region candidates that are a combination of a partial region candidate S1A formed of the living mucous membrane microstructure segment SG1 and a partial region candidate S2A formed of the living mucous membrane microstructure segments SG2 and SG3 (SG2+SG3) illustrated in FIG. 15B, a combination of a partial region candidate S1B formed of the living mucous membrane microstructure segment SG2 and a partial region candidate S2B formed of the living mucous membrane microstructure segments SG3 and SG1 (SG3+SG1) illustrated in FIG. 15C and a combination of a partial region candidate S1C formed of the living mucous membrane microstructure segment SG3 and a partial region candidate S2C formed of the living mucous membrane microstructure segments SG1 and SG2 (SG1+SG2) illustrated in FIG. 15D are determined.

Expression (1) for the aforementioned division condition is applied to the partial region candidates S1A and S2A in FIG. 15B to calculate a value of an objective function $f_{1A}$ in Expression (4) below.

$$f_{1A} = \sigma_{S1A} + \sigma_{S2A} \rightarrow \min \quad (4)$$

Here, $\sigma_{S1A}$ and $\sigma_{S2A}$ are variance values of respective contrasts in the partial region candidates S1A and S2A, respectively, and region division processing is performed so as to minimize the sum of both values according to Expression (4).

Also, for the partial region candidates S1B and S2B in FIG. 15C, a value of an objective function $f_{1B}$ in Expression (5) below is calculated. Here, the partial region candidate S1B corresponds to the living mucous membrane microstructure segment SG2, and the partial region candidate S2B corresponds to the living mucous membrane microstructure segments SG3+SG1.

$$f_{1B} = \sigma_{S1B} + \sigma_{S2B} \rightarrow \min \quad (5)$$

Also, for the partial region candidates S1C and S2C in FIG. 15D, a value of an objective function $f_{1C}$ in Expression (6) below is calculated. Here, the partial region candidate S1C corresponds to the living mucous membrane microstructure segment SG3, and the partial region candidate S2C corresponds to the living mucous membrane microstructure segments SG1+SG2.

$$f_{1C} = \sigma_{S1C} + \sigma_{S2G} \rightarrow \min \quad (6)$$

A combination of partial region candidates S1X and S2X (however, X=A, B or C) that provides a minimum value in the objective functions $f_{1A}$, $f_{1B}$ and $f_{1C}$ in Expressions (4) to (6) above are determined as partial regions (by the division determining section 44c), and based on the result of the determination, the living mucous membrane microstructure is divided into the partial regions.

Calculation to obtain the combination of partial region candidates S1X and S2X that provides a minimum value in the objective function $f_{1A}$, $f_{1B}$ and $f_{1C}$ in Expressions (4) to (6) above is performed, for example, as indicated in FIG. 16A. In step S41, the region division section 43c makes an initial setting of a parameter J (J=1) representing N (N=3 in FIGS. 15A to 15D) partial region candidate combinations. In the case of FIGS. 15A to 15D, J=1 corresponds to a case where the partial region candidates S1A and S2A are designated.

Here, two partial region candidates corresponding to the value of J are indicated by S1J and S2J.

In next step S42, the region division section 43c sets two variance value thresholds σth1 and σth2 for evaluation of division into partial regions. Note that two thresholds σth1 and σth2 are, for example, calculated in advance from, e.g., past data. The two thresholds σth1 and σth2 may be set to upper limit values for allowable variance values for division into partial regions.

In next step S43, the region division section 43c performs processing for dividing the living mucous membrane microstructure segments into two partial region candidates S1J and S2J under the condition that the two partial region candidates S1J and S2J have respective variance values that are equal to or smaller than the two thresholds σth1 and σth2.

In next step S44, the region division section 43c determines whether or not there are partial region candidates S1J and S2J that allow division under the condition that the partial region candidates S1J and S2J have variance values that are equal to or smaller than the two thresholds σth1 and σth2.

If the region division section 43c determines that there are such partial region candidates S1J and S2J, in next step S45, the region division section 43c performs processing for calculating partial region candidates S1Jmin and S2Jmin that provide values allowing the sum of two variance values of the partial region candidate S1J and the partial region candidate S2J to be minimum, and then moves to next step S46.

Also, if there are no such partial region candidates S1J and S2J in the determination processing in step S44, the region division section 43c moves to step S46.

In step S46, the region division section 43c determines whether or not J=N, and if not J=N, in step S47, the region division section 43c increments the value of J by one and returns to the processing in step S43. The above-described processing is repeated from J=1 to J=N as described above. If J=N, in step S48, the region division section 43c calculates partial region candidates S1Jmin and S2Jmin having variance values, the sum of which is minimum in J=1 to N (as S1X and S2X).

Then, the region division section 43c divides the living mucous membrane microstructure segments into the partial region candidates S1Jmin and S2Jmin as partial regions. Here, if no partial region candidates S1Jmin and S2Jmin that provide values allowing the sum of two variance values to be minimum can be calculated at all in step S48 even though the thresholds are set to the upper limit values as described above, region division is performed using another division condition. In this case, a value that is largest in not Expression (1), but, for example, in an objective function $f_{3,J}$ for each set J of the N combinations, which correspond to Expression (3), is obtained.

$$f_{3,J}=(\mu_{S1,J}+\mu_{S2,J})/(\sigma_{S1,J}+\sigma_{S2,J}) \rightarrow \max \quad (7)$$

Furthermore, it is also possible that an objective function that provides a largest value in all of the N combinations is obtained; and division is performed with the partial region candidates in the objective function that provides the largest value as partial regions. FIG. 16B illustrates a flowchart for performing such processing. Here, the processing in FIG. 16B may be performed without the processing illustrated in FIG. 16A being performed. Since the processing in FIG. 16B is similar to the processing in FIG. 16A, only different parts will be described.

First step S41 in FIG. 16B is the same as that of FIG. 16A, and in next step S42', the region division section 43c sets average value thresholds μth1 and μth2 in addition to the variance value thresholds σth1 and σth2 in FIG. 16A. Note that the average value thresholds μth1 and μth2 are, for example, calculated in advance from, e.g., past data.

The two thresholds μth1 and μth2 may be set to respective average value lower limits allowed for division into partial regions. In next step S43', the region division section 43c performs processing for dividing the living mucous membrane microstructure segments into two partial region candidates S1J and S2J under the conditions that respective average values are equal to or larger than the two thresholds μth1 and μth2 and respective variance values are equal to or smaller than the two thresholds σth1 and vth2.

In next step S44, the region division section 43c determines whether or not there are partial region candidates S1J and S2J that allow division under the condition in step S43'.

If the region division section 43c determines that there are such partial region candidates, in next step S45', the region division section 43c performs processing for calculating partial region candidates S1Jmax and S2Jmax having respective variance values, the sum of which is minimum in the partial region candidate S1J and the partial region candidate S2J, and respective average values, the sum of which is maximum in the partial region candidate S1J and the partial region candidate S2J, (in other words, meeting Expression (7)), and then moves to next step S46.

Also, if there are no such partial region candidates S1J and S2J in the determination processing in step S44, the region division section 43c moves to step S46.

In step S46, the region division section 43c determines whether or not J=N, and if not J=N, in step S47, the region division section 43c increments the value of J by one and returns to step S43. The above-described processing is repeated from J=1 to J=N. If J=N, in step S48', the region division section 43c calculates partial region candidates S1Jmax and S2Jmax having respective variance values, the sum of which is minimum in J=1 to N, and respective average values, the sum of which is maximum in J=1 to N (in other words, meeting Expression (7) in all the N combinations) (as S1X and S2X).

Then, the region division section 43c divides the living mucous membrane microstructure segments into the partial region candidates S1Jmax and S2Jmax as partial regions.

According to the present embodiment, the above-described region division processing is performed using image data generated by the image data generating section 41a, enabling living mucous membrane microstructures appearing as a continuous pattern in the image data to be divided into respective partial regions in which respective contrasts exhibit continuity. As a result, the accuracy of extraction of living mucous membrane microstructures corresponding to findings can be enhanced.

In other words, if three-dimensional living mucous membrane microstructures appear as a continuous pattern in two-dimensional image data resulting from pickup of an image of the living mucous membrane microstructures, the pattern can be divided into partial regions by a boundary exhibiting discontinuity corresponding to the three-dimensional structures, and in each of the partial regions, contrasts exhibit continuity after the division. As a result, the extraction accuracy for extracting partial regions corresponding to three-dimensional living mucous membrane microstructures can be enhanced.

Note that although the present embodiment has been described in terms of a case of division into two partial structures, the division number is not specifically limited.

Also, the present embodiment is not limited to cases of a trifurcated structure such as illustrated in FIGS. 15A to 15D, and even a structure divaricated into four or more parts can be divided into regions by processing and method similar to the above.

Also, the region division processing according to the present embodiment is not limited to that according to the method in which a combination of living mucous membrane microstructure segments that minimize the value of the objective function $f_1$ (or the equivalent objective function $f_{1A}$, $f_{1B}$ or $f_{1C}$) in Expression (1) (or any of equivalent Expressions (4) to (6)) is obtained, and may be that according to the method in which a combination of living mucous membrane microstructure segments that maximize the value of the objective function $f_2$ in Expression (2) is obtained, and furthermore, as described above, may be that according to the method in which a combination of living mucous membrane microstructure segments that maximize the value of the objective function $f_3$ in Expression (3) is obtained.

Also, the region division processing according to the present embodiment is not limited to that performed for an image where the narrow-band light observation mode is selected, and can also be performed in a manner substantially similar to the above for, for example, an image obtained where the normal light observation mode is selected.

Furthermore, the region division processing according to the present embodiment is not limited to that according to the method in which an evaluation value representing a linear structure closeness based on an eigenvalue obtained by calculation of an eigenvalue of a Hessian matrix as a filter that enhance a linear structure, and may be a filter for where a line segment is a structure element, calculating a difference between an average value of image density values in the structure element and an average value in a local region surrounding the structure element. Also, the region division processing may be one in which a difference value provided by elliptical Gaussian filter is calculated or may be one in which a Laplacian provided by elliptical Gaussian filter is calculated. Also, a differential filter such as Sobel filter may be used.

Also, the region division processing according to the present embodiment is not limited to one in which response values of a filter that enhances a linear structure are calculated as predetermined feature values, using pixel values of image data corresponding to G light, and may be one in which such calculation is performed using pixel values of image data corresponding to, for example, R light or B light.

Also, the region division processing according to the present embodiment may be one in which response values of a filter that enhances a linear structure are calculated as predetermined feature values, using values obtained by dividing pixel values according to G light by image density values (or pixel values) in image data corresponding to R light.

Furthermore, the region division processing according to the present embodiment may be one in which response values of a filter that enhances a linear structure are calculated as predetermined feature values, using values after conversion of pixel values in the RGB color system into those in the HSI color system or the L*a*b color system.

Also, the region division processing according to the present embodiment is not limited to one in which under the region division condition in which variation is minimum in partial regions resulting from division, variance is used as a parameter for variation, and may be one in which a standard deviation or a variation coefficient obtained by dividing a standard deviation by an average is used.

Also, the region division processing according to the present embodiment is not limited to one in which under the region division condition that variation between partial regions resulting from division is maximum, an average value is used as a parameter for a statistical nature, and may be one in which a central value or a mode value is used.

Also, the region division processing according to the present embodiment may be one in which a divarication portion is identified by a response value of a matched filter modeled so as to conform to a divarication shape.

(Second Embodiment)

Next, a second embodiment of the present invention will be described. While the first embodiment has been described in terms of means and method for dividing living mucous membrane microstructures to regions based on contrast discontinuity (or inhomogeneity), the spirit of the present embodiment is not limited to the method in which region division is performed based on contrast discontinuity or inhomogeneity, and for example, region division can also be performed based on a morphological feature of a structure.

Furthermore, while in the first embodiment, response values of a filter that enhances a linear structure, which are feature values to be used for extraction of a living mucous membrane microstructure, and contrasts are correlated with each other and same feature values are thus used in both living mucous membrane microstructure extraction and region division into partial regions, different feature values can be used in living mucous membrane microstructure extraction and region division into partial regions.

Thus, in the present embodiment, a medical image processing apparatus and a medical image processing method that can perform region division based on morphological feature values such as widths of a pattern of a living mucous membrane microstructure while different feature values are used in living mucous membrane microstructure extraction and region division into partial regions will be described.

Note that an endoscope apparatus according to the present embodiment has a configuration that is the same as that of the endoscope apparatus 1 according to the first embodiment illustrated in FIG. 1. Thus, for the endoscope apparatus according to the present embodiment, reference numerals that are the same as those of the endoscope apparatus 1 according to the first embodiment are used and a description of the configuration will be omitted.

Also, an image processing section included in the medical image processing apparatus according to the present embodiment has a configuration that is the same as that of the image processing section 41 in FIG. 1. Thus, reference numerals that are the same as those in the image processing section 41 according to the first embodiment are used for the image processing section according to the present embodiment, and description thereof will be omitted. A configuration of an arithmetic operation section 41b according to the present embodiment is illustrated in FIG. 16C.

The arithmetic operation section 41b according to the present embodiment illustrated in FIG. 16C is partially different from the arithmetic operation section 41b according to the first embodiment illustrated in FIG. 5. While common feature values are used by the feature value calculating section 43a in FIG. 5 both when the feature value calculating section 43a extracts a living mucous membrane microstructure and when the feature value calculating section 43a performs region division, the feature value calculating section 43a in FIG. 16C includes an extraction feature value calculating section 45a that calculates feature values for extracting a living mucous membrane microstructure, and a region division feature value calculating section 45b that calculates feature values to be used when region division is performed. Here, the arithmetic operation section 41b in FIG. 16C has a configuration including that of the first embodiment, and can calculate common feature values as in the first embodiment.

Also, while in the first embodiment illustrated in FIG. 5, contrast discontinuity (or inhomogeneity) is used as a division condition for division into partial regions, the present embodiment includes a division condition setting section 43d that sets (or selects) a division condition so that discontinuity of morphological feature values of a structure can be set as a division condition in addition to contrast. Here, the division condition setting section 43d may be provided in, e.g., an inner portion of the image processing section 41 outside the arithmetic operation section 41b.

As illustrated in FIG. 16C, the arithmetic operation section 41b includes a memory 47 storing a first division condition 46a for setting contrast discontinuity (or inhomogeneity) as a division condition, and a second division condition 46b for setting a morphological feature value discontinuity (or inhomogeneity) in a structure as a division condition. Here, the memory 47 may be provided in, e.g., the inner portion of the image processing section 41 outside the arithmetic operation section 41b.

Then, the division condition setting section 43d is configured so as to be able to, upon a selection instruction provided by a user, select one of the first division condition 46a and the second division condition 46b stored in the memory 47 to set a division condition. In the present embodiment, the division condition setting section 43d can further select a third division condition 46c. The third division condition is intended to set color tone discontinuity (or inhomogeneity) as a division condition. The other components are similar to those of the first embodiment.

Next, an operation of an endoscope apparatus 1 according to the present embodiment will be described.

Since the present embodiment is substantially similar to the first embodiment if the first division condition is selected as a division condition, a case where a division condition other than the first division condition is selected will be described.

In other words, the below description will be provided for a case where the arithmetic operation section 41b includes the feature value calculating section 43a including the extraction feature value calculating section 45a and the region division feature value calculating section 45b, an extraction section 43b, a region division section 43c including a divarication portion identifying section 44a, a segment division section 44b and a division determining section 44c, and a division condition setting section 43d that can select the second division condition 46b or the third division condition 46c. Here, as a modification of the second embodiment, a configuration including such arithmetic operation section 41b may be provided. Note that in the case of the configuration according to the modification of the second embodiment, an operation of the configuration does not include the first embodiment using contrasts. On the other hand, an operation of the configuration illustrated in FIG. 16C includes the below-described operation in addition to the operation of the first embodiment.

First, a surgeon powers on the respective sections of the endoscope apparatus 1, and then selects the normal light observation mode via an observation mode selection switch 24. Then, the surgeon inserts an endoscope 2 into a body cavity while viewing an image displayed on a display apparatus 5 when the normal light observation mode is selected, that is, an image having colors substantially similar to those of a case where a target object is viewed by the naked eye, thereby bringing a distal end portion 21b close to a site where an observation target body tissue 101 exists.

Upon selection of the normal light observation mode via the observation mode selection switch 24, light of respective colors, i.e., R light, G light and B light are sequentially emitted from a light source apparatus 3 to the body tissue 101, and in the endoscope 2, a respective image corresponding to the light of each color is obtained.

Figure 17:
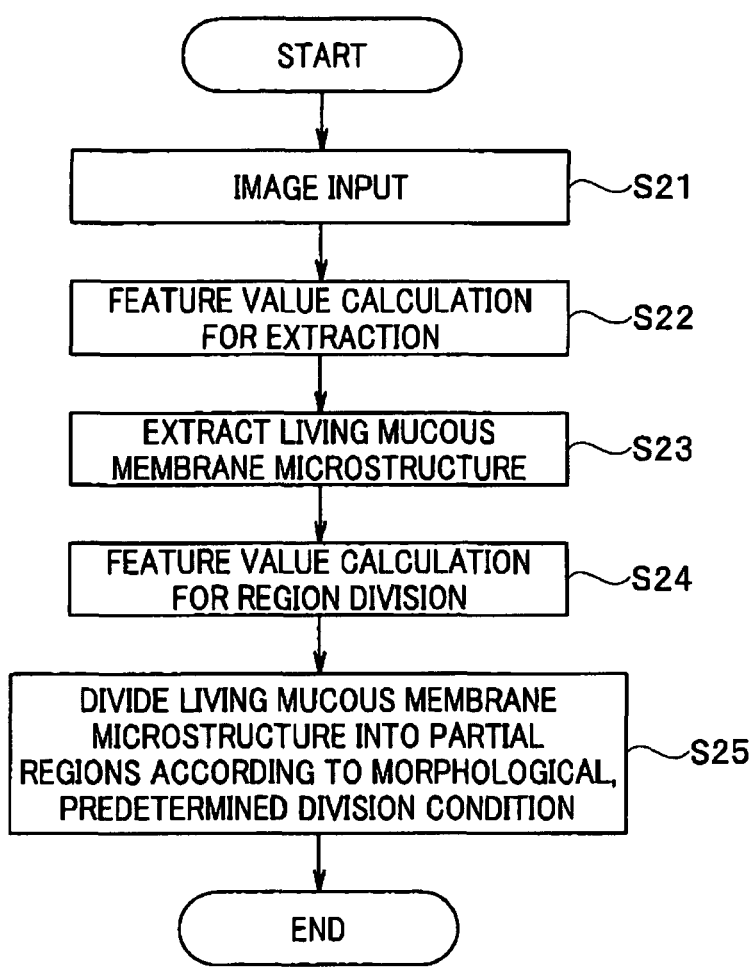
FIG. 17 is a flowchart illustrating an example of processing performed in an image processing section in the second embodiment of the present invention.

FIG. 17 illustrates main processing performed by the image processing section 41 in the present embodiment, the processing being different from that of the first embodiment.

As indicated in step S21 in FIG. 17, the image data generating section 41a in the image processing section 41 receives an input of the image corresponding to the R light, the image corresponding to the G light, and the image corresponding to the B light via an image input section 41d. Then, the image data generating section 41a generates respective image data of a color component corresponding to each image, and outputs the generated image data to the arithmetic operation section 41b in the image processing section 41.

The arithmetic operation section 41b in the image processing section 41 may, as necessary, perform inverse gamma correction and/or noise suppression processing as non-illustrated in preprocessing, based on the image data generated by the image data generating section 41a.

Based on the image data generated by the image data generating section 41a, (the feature value calculating section 43a in) the arithmetic operation section 41b calculates predetermined feature values to be used for subsequent processing. In the present embodiment, as indicated in step S22 in FIG. 17, the feature value calculating section 43a calculates a response value of a filter that enhances a linear structure for each pixel of the image data according to the G light, using the extraction feature value calculating section 45a, and thereby calculates feature values for extraction. Then, the feature value calculating section 43a sends the extracted feature values to the extraction section 43b in the arithmetic operation section 41b.

Based on the feature values extracted in step S22, as indicated in step S23 in FIG. 17, the extraction section 43b performs processing for extracting a region where a living mucous membrane microstructure exists in the body tissue 101.

Furthermore, in step S24, (the feature value calculating section 43a in) the arithmetic operation section 41b calculates feature values for region division, which are different from the feature values for extraction calculated in step S22.

In other words, the feature value calculating section 43a calculates, for example, morphological feature values (for a specific example, widths) of a pattern of the living mucous membrane microstructure extracted in step S23, as feature values for region division, using the region division feature value calculating section 45b.

Figure 18A:
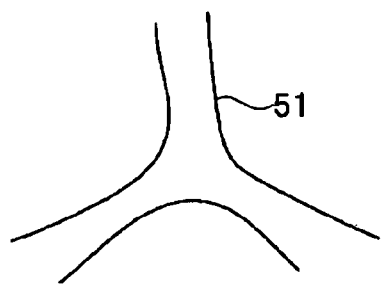
FIG. 18A is a schematic diagram for describing an example of a method of calculation of a width of a living mucous membrane microstructure.
Figure 18B:
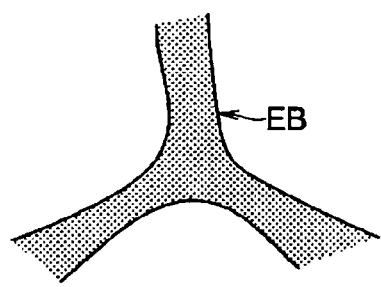
FIG. 18B is a schematic diagram for describing an example of a method of calculation of a width of a living mucous membrane microstructure.

A specific width calculation method will be described with reference to FIGS. 18A to 18G. First, the region division feature value calculating section 45b binarizes a living mucous membrane microstructure 51 illustrated in FIG. 18A, which has been extracted in step S23 in FIG. 17. FIG. 18B illustrates a binary image EB resulting from the binarization.

Here, the binary image EB is an image in which a pixel value of each pixel for the living mucous membrane microstructure is 1 and a pixel value of each pixel other than those pixels is 0.

Figure 18C:
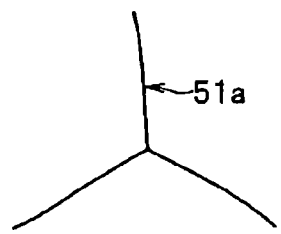
FIG. 18C is a schematic diagram for describing an example of a method of calculation of a width of a living mucous membrane microstructure.

Furthermore, the region division feature value calculating section 45b performs thinning processing for center line detection on the binary image EB, thereby obtains a thinned image 51a illustrated in FIG. 18C. The thinned image 51a is an image in which a pixel value of each of the pixels for the center lines of the living mucous membrane microstructure is 1 and a pixel value of each of the other pixels is 0.

Figure 18D:
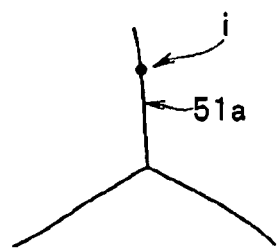
FIG. 18D is a schematic diagram for describing an example of a method of calculation of a width of a living mucous membrane microstructure.
Figure 18E:
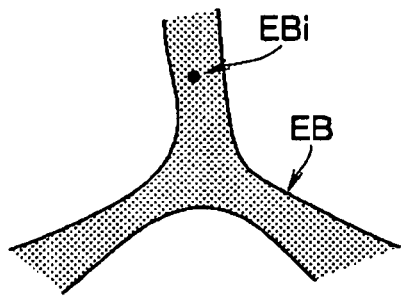
FIG. 18E is a schematic diagram for describing an example of a method of calculation of a width of a living mucous membrane microstructure.

As illustrated in FIG. 18D, where i is a position of each of the pixels having the pixel value of 1 in the thinned image 51a (1≤i<ISX×ISY|Si=1), as illustrated in FIG. 18E, the width of the living mucous membrane microstructure in the pixel EBi in the binary image EB for each of the positions i. Here, (1≤i<ISX×ISY|Si=1) above represents a position i where the pixel value Si is 1 in ISX×ISY.

Figure 18F:
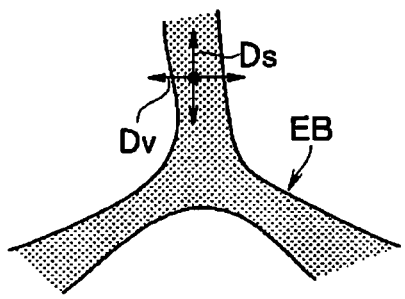
FIG. 18F is a schematic diagram for describing an example of a method of calculation of a width of a living mucous membrane microstructure.

FIG. 18F illustrates a running direction Ds of the living mucous membrane microstructure and an orthogonal direction Dv orthogonal to the running direction Ds for calculating the width of the living mucous membrane microstructure in the pixel EBi in the binary image EB.

Figure 18G:
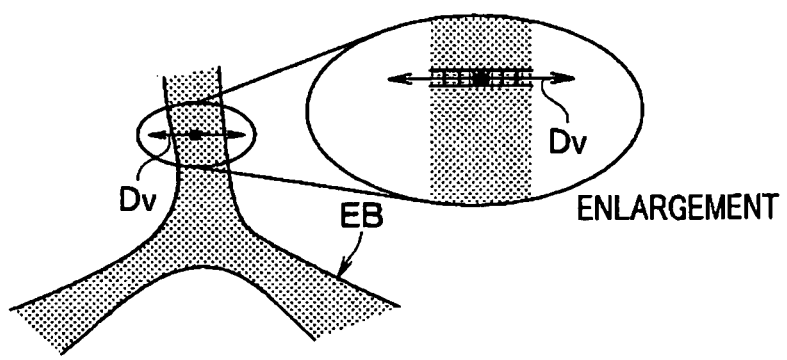
FIG. 18G is a schematic diagram for describing an example of a method of calculation of a width of a living mucous membrane microstructure.

The width of the living mucous membrane microstructure corresponds to, for example, the number of continuous pixels having a pixel value of 1 in the binary image EB in the orthogonal direction Dv orthogonal to the running direction Ds of the living mucous membrane microstructure in the pixel EBi. Then, as illustrated in FIG. 18G, the count M of continuous pixels having a pixel value of 1 in the orthogonal direction Dv of the binary image EB is calculated. In the case of FIG. 18G, the width has a value corresponding to M=7.

Here, the running direction Ds of the living mucous membrane microstructure in the pixel EBi can be obtained by a known method such as described below.

For example, the running direction Ds can be obtained by performing horizontal differential processing and vertical differential processing on the image data corresponding to the G light, and quantizing a gradient direction θ obtained by calculating arc tangents of the resulting differential values in the two directions, for example, in four directions such as illustrated in FIG. 19.

The left side of FIG. 19 indicates quantization of the gradient direction θ in four directions D1 to D4 where −π≤θ≤π in a direction from the −π radian to the π radian, in units of a (π/4) radian. Also, the right side of FIG. 19 indicates the range of the gradient direction θ for each of the four directions.

Also, the orthogonal direction Dv orthogonal to the running direction Ds of the living mucous membrane microstructure at the pixel EBi can be obtained by adding a (π/2) radian to the gradient direction θ obtained by calculating the arc tangents of the differential values in the two directions, which can be obtained by the above-described calculation, and further quantizing the resulting direction, for example, in four direction such as indicated in FIG. 19. Note that the number of directions of the quantization is not limited to four directions such as illustrated in FIG. 19 and may be a plural number that is no less than 4.

Figure 20:
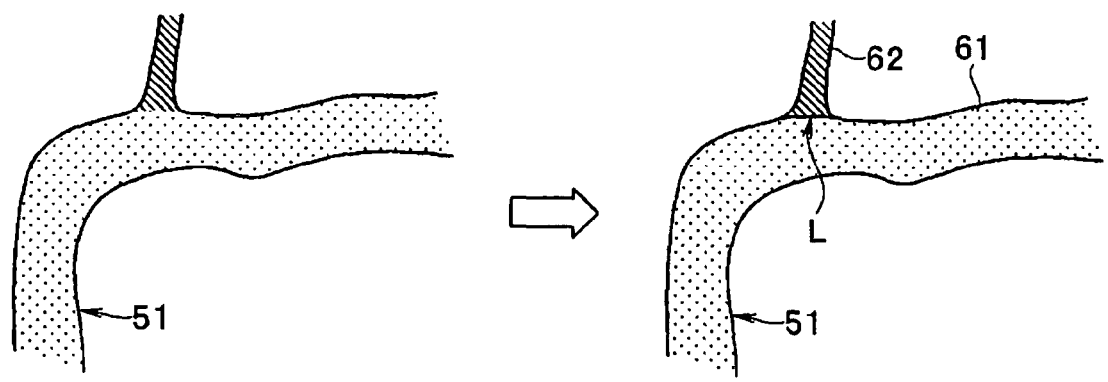
FIG. 20 is a schematic diagram illustrating an example in which a predetermined division condition for division into regions relates to thickness.

Furthermore, for example, if it is determined in step S24 in FIG. 17 that there is a region having different widths (or thicknesses) as morphological feature values calculated in a living mucous membrane microstructure 51 as illustrated in FIG. 20, the region division section 43c in the arithmetic operation section 41b, as indicated in step S25, divides the region into partial regions 61 and 62 by a division line L based on the condition that the region exhibits width discontinuity or inhomogeneity (morphological, predetermined division condition). Then, the widths of the regions 61 and 62 resulting from the division each exhibit continuity or homogeneity.

Here, the region division processing is processing similar to the region division processing according to the first embodiment described above, and processing similar to that of the first embodiment can be performed by replacing contrasts with widths.

According to the present embodiment, the above-described region division processing is performed using image data generated by the image data generating section 41a, enabling living mucous membrane microstructures appearing as a continuous pattern on image data to be divided into two partial regions in which the respective living mucous membrane microstructures each have a uniform width. As a result, the accuracy of extraction of living mucous membrane microstructures according to findings can be enhanced.

In other words, if three-dimensional living mucous membrane microstructures appear as a continuous pattern on two dimensional image data resulting from image pick up of the living mucous membrane microstructures, the pattern can be divided into partial regions by a boundary exhibiting the discontinuity according the three-dimensional structures, each of the partial regions having a uniform or continuous width. As a result, the accuracy of extraction of partial regions corresponding to three-dimensional living mucous membrane microstructures can be enhanced.

Note that the region division processing based on the morphological division condition in the present embodiment is not limited to that using widths of living mucous membrane microstructures for division into partial regions, and the third division condition 46c (condition relating to color tone) illustrated in FIG. 16C may be selected to perform region division processing with color tone discontinuity (or inhomogeneity) employed as a predetermined division condition.

Figure 21:
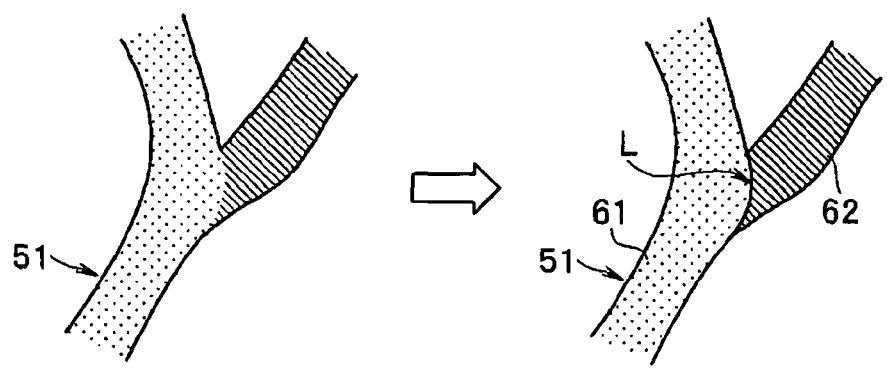
FIG. 21 is a schematic diagram illustrating an example in which a predetermined division condition for division into regions relates to color tone.

FIG. 21 illustrates an example in which a living mucous membrane microstructure 51 is divided into partial regions 61 and 62 by a division line L based on color tone discontinuity in the living mucous membrane microstructure 51.

In other words, as feature values relating to color tone, for example, image data density values in the image data corresponding to the G light at respective pixel positions in the living mucous membrane microstructure extracted in step S23 in FIG. 17 may be calculated in step S24. Also, by a method substantially similar to the above-described method, living mucous membrane microstructure segments are detected and an average value is calculated for each of all pixels included in each segment from the image density values of the image data corresponding to the G light, enabling obtainment of color tones in each living mucous membrane microstructure segment.

Figure 22:
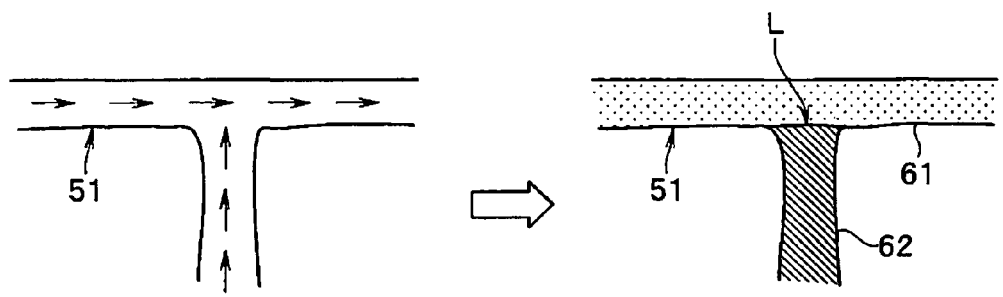
FIG. 22 is a schematic diagram illustrating an example in which a predetermined division condition for division into regions relates to running direction.
Figure 23:
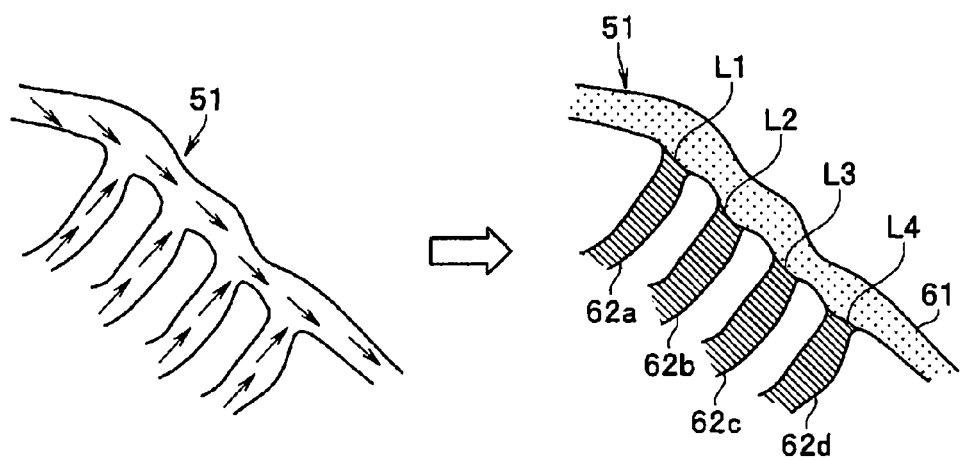
FIG. 23 is a schematic diagram illustrating an example in which a predetermined division condition for division into regions relates to running direction.

Also, the region division processing according to the present embodiment is not limited to that using widths of living mucous membrane microstructures for dividing the living mucous membrane microstructures into partial regions, and as illustrated in FIGS. 22 and 23, may be that using running directions of living mucous membrane microstructures. FIG. 22 illustrates division of parts of a living mucous membrane microstructure 51 in which respective running directions are different from each other as illustrated on the left side of the Figure into partial regions 61 and 62 by a division line L as illustrated on the right side of the Figure. Also, FIG. 23 illustrates division of parts of a living mucous membrane microstructure 51 in which respective running directions are different from each other as illustrated on the left side of the Figure into partial regions 61, 62a, 62b, 62c and 62d by division lines L1, L2, L3 and L4 on the right side of the Figure.

As described above, a running direction at each pixel position of a living mucous membrane microstructure, can be obtained by subjecting image data corresponding to G light to horizontal differential processing and vertical differential processing, and quantizing a gradient direction θ obtained by calculating arc tangents of differential values for the two directions obtained as a result of the processing, for example, in four directions such as illustrated in FIG. 19.

Also, a direction of each living mucous membrane microstructure segment can be obtained by detecting living mucous membrane microstructure segments by a method substantially similar to the above and calculating a mode value from running directions of all pixels included in each segment. Then, if the mode values of the running directions exhibit discontinuity, the living mucous membrane microstructure segments are divided into partial regions.

Figure 24A:
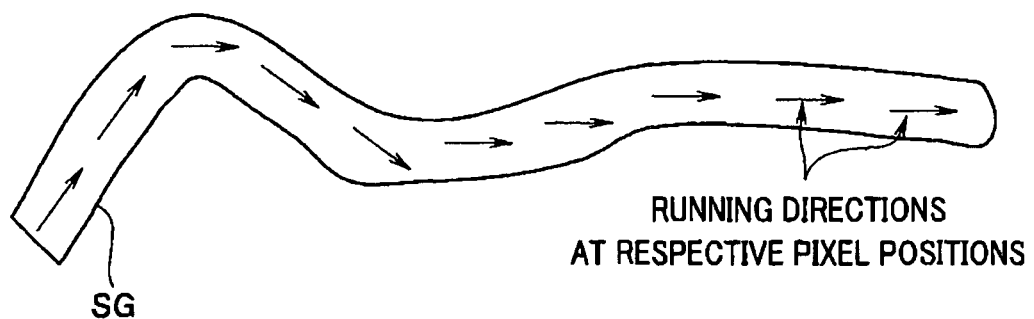
FIG. 24A is a diagram for describing an example of a method of calculation of a running direction of a living mucous membrane microstructure segment.
Figure 24B:
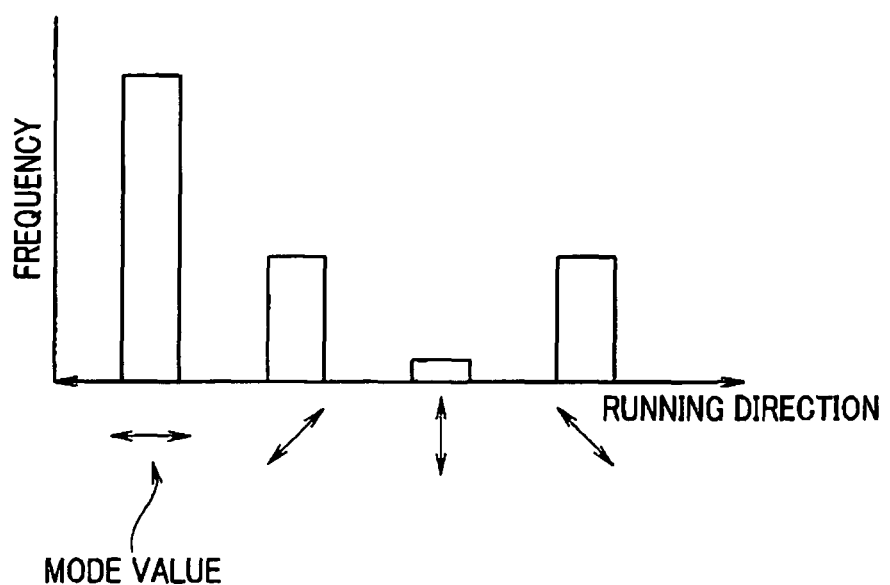
FIG. 24B is a diagram for describing an example of a method of calculation of a running direction of a living mucous membrane microstructure segment.

A process of running direction frequency calculation for a living mucous membrane microstructure segment is illustrated in FIGS. 24A and 24B. As illustrated in FIG. 24A, a running direction at each pixel position in a living mucous membrane microstructure segment SG is calculated. Note that information on the calculated running directions of all the pixels is categorized into, for example, the four directions D1 to D4 illustrated in FIG. 19 and a frequency of each of the categorized running directions is calculated. Values of calculated frequencies of the respective directions are illustrated in FIG. 24B, whereby a mode value of the running directions in the living mucous membrane microstructure segment SG can be calculated. Then, the running direction mode value is set as the running direction. Subsequently, using the running direction mode value, region division processing is performed with discontinuity of the running direction mode values employed as a division condition. Then, after the division, the running direction mode values substantially exhibit continuity in each partial region.

Note that the region division processing according to the present embodiment is not limited to the case where region division processing is performed using mode values, and region division processing may be performed using weighted mode values in a weighted histogram obtained by multiplying each gradient direction by a gradient strength for weight.

Also, the region division processing according to the present embodiment is not limited to that using widths of living mucous membrane microstructures for division into partial regions, and may be that using lengths of living mucous membrane microstructures.

A length of a living mucous membrane microstructure is, for example, the total number of pixels having a pixel value of 1 in a thinned image obtained by binarizing the living mucous membrane microstructure extracted in step S23 in FIG. 17 and subjecting the living mucous membrane microstructure to thinning processing for center line detection.

Also, a length of each living mucous membrane microstructure segment can be calculated by detecting thinned segments from a thinned image by means of a method substantially similar to the above and counting the number of pixels included in each thinned segment.

Furthermore, the region division processing according to the present embodiment is not limited to that using widths of living mucous membrane microstructures for division into partial regions, and may be that using a combination of two or more of contrast, width, color tone, running direction and length in the living mucous membrane microstructures. An example of region division using width and color tone as an example combination is indicated below focusing only on main parts of the processing, which are key points for the processing, with parts of the processing similar to the above omitted.

For example, as illustrated in FIG. 11 referred to above, when a region A is divided into two regions (a partial region C and a partial region D), where $\sigma_{wC}$ is a variance value of widths in the partial region C, $\sigma_{cC}$ is a variance value of color tones in the partial region C, $\sigma_{wD}$ is a variance value of widths in the partial region D and $\sigma_{cD}$ is a variance value of color tones in the partial region D, the partial region C and the partial region D that minimize the below objective function $f_{1D}$ may be obtained. Here, each of $\alpha$ and $\beta$ is a constant representing weight, and here, for example, $\alpha=1$ and $\beta=1$.

$$f_{1D}=\alpha(\sigma_{wC}+\sigma_{wD})+\beta(\sigma_{cC}+\sigma_{cD}) \to \min \quad (8)$$

Also, for example, as illustrated in FIG. 11, when a region A is divided into two regions (a partial region C and a partial region D), where $\mu_{wC}$ is an average value of width in the partial region C, $\mu_{cC}$ is an average value of color tones in the partial region C, $\mu_{wD}$ is an average value of widths in the partial region D and $\mu_{cD}$ is an average value of color tones in the partial region D, the partial region C and the partial region D that maximize the below objective function $f_{2B}$ may be obtained. Here, each of $\alpha$ and $\beta$ is a constant representing weight, and here, for example, $\alpha=1$ and $\beta=1$.

$$f_{2B}=\alpha(\mu_{wC}+\mu_{wD})+\beta(\mu_{cC}+\mu_{cD}) \to \max \quad (9)$$

Furthermore, for example, as illustrated in FIG. 11, when a region A is divided into two regions (a partial region C and a partial region D), where $\sigma_{wC}$ is a variance value of widths in the partial region C, $\sigma_{cC}$ is a variance value of color tones in the partial region C, $\mu_{wC}$ is an average value of widths in the partial region C, $\mu_{cC}$ is an average value of color tones in partial region C, $\sigma_{wD}$ is a variance value of widths in the region D, $\sigma_{cD}$ is a variance value of color tones in the region D, $\mu_{wD}$ is an average value of widths in the partial region D and $\mu_{cD}$ is an average value of color tones in the partial region D, the partial region C and the partial region D that maximize the below objective function $f_{3B}$ may be maximized.

Here, each of $\alpha$ and $\beta$ is a constant representing weight, and here, for example, $\alpha=1$ and $\beta=1$.

$$f_{3B}=\alpha(\mu_{wC}+\mu_{wD})/(\sigma_{wC}+\sigma_{wD})+\beta(\mu_{cC}+\mu_{cD})/(\sigma_{cC}+\sigma_{cD}) \to \max \quad (10)$$

The region division processing according to the present embodiment may be that according to a method in which a combination of living mucous membrane microstructure segments that minimize the value of the objective function $f_{1D}$ in Expression (8) is obtained, that according to a method in which the value of the objective function $f_{2B}$ in Expression (9) is maximized or may be one in which the value of the objective function $f_{3B}$ in Expression (10) is maximized.

(Third Embodiment)

Next, a description of a third embodiment of the present invention will be provided. The description of the present embodiment will be provided on region division processing based on saliencies of living mucous membrane microstructures, which is different from the first embodiment and the second embodiment in which region division processing is performed based on a division condition to provide respective partial regions resulting from division holding continuity or sameness.

In other words, while the first embodiment and the second embodiment employ a method in which region division is performed focusing on feature change in each region or between regions of partial regions, the present embodiment employs a method in which region division is performed focusing on absolute values of features of partial regions. More specifically, where a living mucous membrane microstructure is divided into regions, the living mucous membrane microstructure is divided into a partial region in which a predetermined feature value is maximum (salient partial region) and a partial region other than that partial region.

Figure 25:
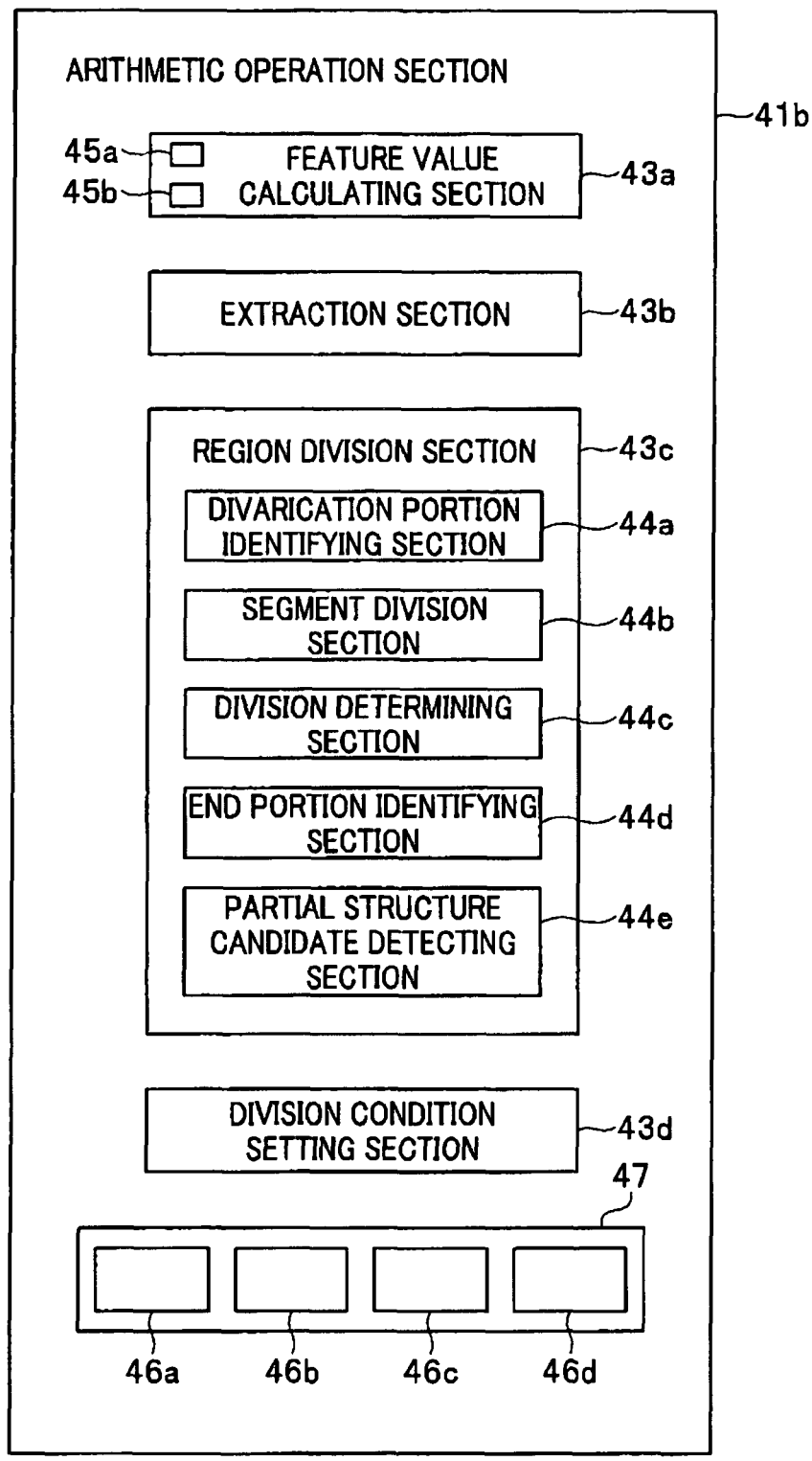
FIG. 25 is a block diagram illustrating a main configuration of an arithmetic operation section in a third embodiment of the present invention.

Here, in the present embodiment, processing is performed using an endoscope apparatus 1 having a configuration similar to those of the first embodiment and the second embodiment. Thus, in the present embodiment, an endoscope apparatus 1 provided with reference numerals that are the same as those of the first embodiment will be used. Also, an image processing section according to the present embodiment has a configuration that is the same as the image processing section 41 of the first and second embodiments, and the present embodiment will be described using an image processing section 41 provided with reference numerals that are the same as those of the image processing section 41 of the first and second embodiment. Also, FIG. 25 illustrates a configuration of an arithmetic operation section 41b in the present embodiment. The arithmetic operation section 41b illustrated in FIG. 25 is the arithmetic operation section 41b illustrated in FIG. 16C in which a fourth division condition 46d for performing region division processing based on saliency is further stored in the memory 47. Then, a user can select an arbitrary division condition from the first division condition 46a to the fourth division condition 46d.

A region division section 43c further includes: an end portion identifying section 44d, which serves as end portion identifying means for identifying (or detecting) at least one end portion of a living mucous membrane microstructure extracted by an extraction section 43b, and a partial structure candidate detecting section 44e, which serves as partial structure candidate detecting means for detecting, based on the end portion identified by the end portion identifying section 44d, a partial structure including the end portion as an end thereof, as a partial structure candidate from the living mucous membrane microstructure extracted by the extraction section 43b.

Then, a division determining section 44c in the region division section 43c, based on feature values calculated from each partial structure candidate detected by the partial structure candidate detecting section 44e, performs determination of partial regions according to the fourth division condition 46d as predetermined division condition and performs division into the partial regions.

Note that the partial structure candidate detecting section 44e may be configured to double as the end portion identifying section 44d. In other words, the partial structure candidate detecting section 44e may identify at least one end portion from a living mucous membrane microstructure, and based on the result of the identification, (the partial structure candidate detecting section 44e) further detect a partial structure having the end portion as an end thereof as a partial structure candidate.

If a user selects a division condition other than the fourth division condition, the operation may be similar to that of the second embodiment. Thus, the below description will be provided in terms of a case where a user selects the fourth division condition.

A main part of the present embodiment is different from those of the first embodiment and the second embodiment mainly in feature value used for region division into partial regions and a criterion for region division. Thus, the present embodiment will be described mainly in terms of the parts that are different from those of the first embodiment and the second embodiment and description of parts similar to those of the first embodiment and the second embodiment will be omitted as appropriate.

In other words, the below description will be provided on in terms of the arithmetic operation section 41b including a feature value calculating section 43a that includes an extraction feature value calculating section 45a and a region division feature value calculating section 45b, an extraction section 43b, a region division section 43c including the end portion identifying section 44d, the partial structure candidate detecting section 44e and the division determining section 44c, and a division condition setting section 43d in which the fourth division condition 46d is selected. Also, as a modification of the third embodiment, a configuration including such arithmetic operation section 41b only will be employed.

Next, an operation of the endoscope apparatus 1 according to the present embodiment will be described.

First, a surgeon powers on the respective sections of the endoscope apparatus 1 and then selects the normal light observation mode via the observation mode selection switch 24. Then, the surgeon inserts the endoscope 2 into a body cavity while viewing an image displayed on a display apparatus 5 when the normal light observation mode is selected, that is, an image of colors substantially similar to those of a case where a target object is viewed by the naked eye, thereby bringing a distal end portion 21b close to a site where an observation target body tissue 101 exists.

Upon selection of the normal light observation mode via the observation mode selection switch 24, light of respective colors, i.e., R light, G light and B light are sequentially emitted from a light source apparatus 3 to the body tissue 101, and in the endoscope 2, a respective image corresponding to the light of each color is obtained.

Figure 26:
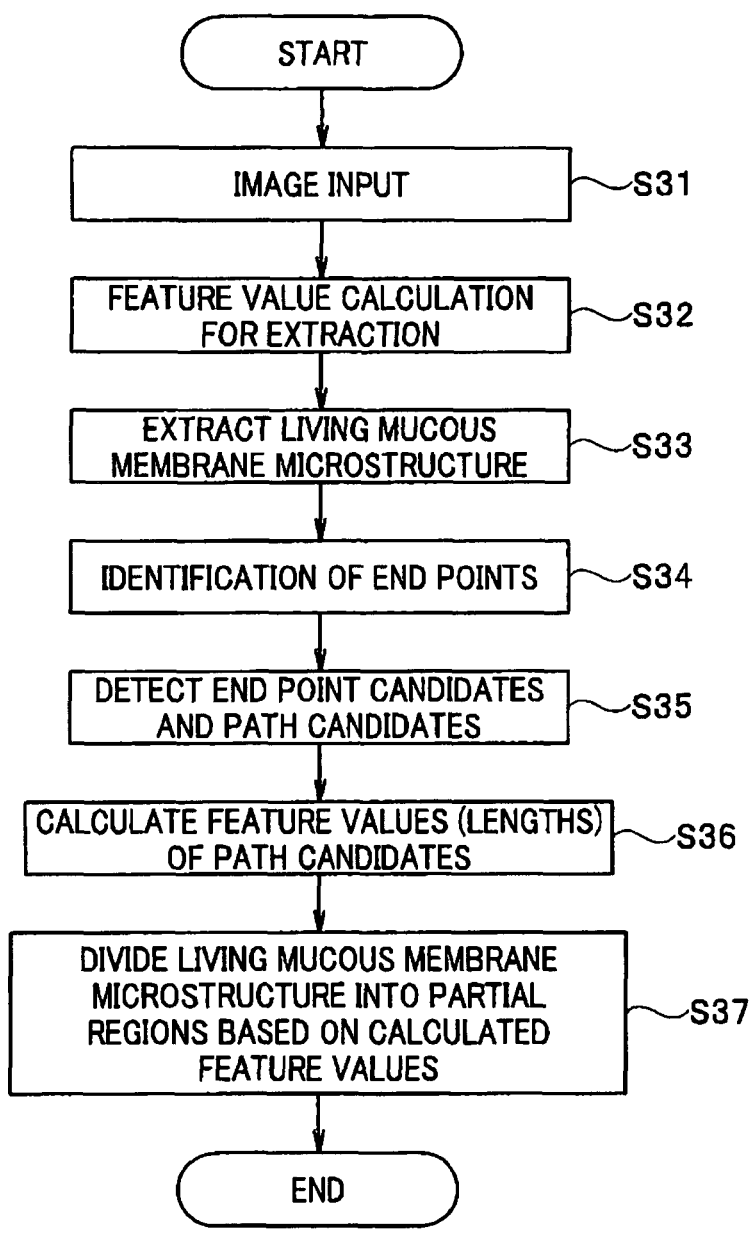
FIG. 26 is a flowchart for an example of processing performed in an image processing section in the third embodiment of the present invention.

FIG. 26 illustrates main processing performed by the image processing section 41 in the present embodiment.

An image data generating section 41a in the image processing section 41 receives an input of the image corresponding to the R light, the image corresponding to the G light and the image corresponding to the B light via the image input section 41d, as indicated in step S31 in FIG. 26. Then, the image data generating section 41a generates respective image data of a color component corresponding to each image, and outputs the generated image data to the arithmetic operation section 41b in the image processing section 41.

The arithmetic operation section 41b in the image processing section 41 may, as necessary, perform inverse gamma correction and/or noise suppression processing as non-illustrated preprocessing, based on the image data generated by the image data generating section 41a.

Based on the image data generated by the image data generating section 41a, (the feature value calculating section 43a of) the arithmetic operation section 41b calculates predetermined feature values to be used for subsequent processing. In the present embodiment, as indicated in step S32 in FIG. 26, the feature value calculating section 43a calculates a response value of a filter that enhances a linear structure for each pixel of the image data corresponding to the G light and thereby calculates feature values for exaction using the extraction feature value calculating section 45a. Then, the feature value calculating section 43a sends the extracted feature values to the extraction section 43b in the arithmetic operation section 41b.

Based on the feature values extracted in step S32, as indicated in step S33 in FIG. 26, the extraction section 43b performs processing for extracting a region where a living mucous membrane microstructure exists in the body tissue 101. The extraction section 43b outputs the extracted living mucous membrane microstructure to the region division section 43c. As indicated in step S34, the end portion identifying section 44d in the region division section 43c identifies a plurality of end points from the extracted living mucous membrane microstructure (as end portions of the living mucous membrane microstructure). The processing in step S34 onwards will be described with reference to FIGS. 27A to 27I.

As indicated in step S34 in FIG. 26, the end portion identifying section 44d in the region division section 43c identifies a plurality of end points from the living mucous membrane microstructure extracted in step S33, and in next step S35, the partial structure candidate detecting section 44e in the region division section 43c detects two end point sets as end point candidates and detects a path running through a living mucous membrane microstructure connecting both end points as a path candidate (forming a partial structure candidate) for each of the detected sets.

Figure 27A:
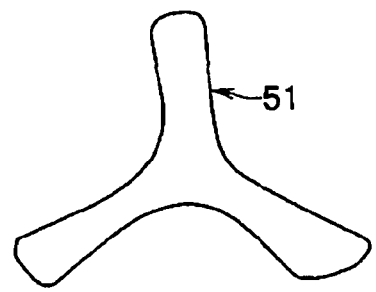
FIG. 27A is a schematic diagram for describing an example in which a living mucous membrane microstructure is divided into partial regions according to a predetermined division condition based on saliency.
Figure 27B:
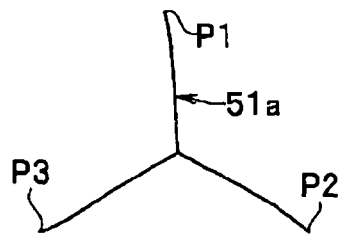
FIG. 27B is a schematic diagram for describing an example in which a living mucous membrane microstructure is divided into partial regions according to a predetermined division condition based on saliency.

More specifically, the end portion identifying section 44d binarizes a living mucous membrane microstructure 51 illustrated in FIG. 27A and further subjects the resulting living mucous membrane microstructure 51 to thinning processing for center line detection, thereby generating a thinned image 51a illustrated in FIG. 27B. Also, the end portion identifying section 44d identifies all of pixels each having only one pixel adjacent thereto as an end point from the thinned image 51a, that is, an end point group. In the case of FIG. 27B, three end points P1, P2 and P3 are identified (detected), and the end point group includes the end points P1, P2 and P3.

Next, the partial structure candidate detecting section 44e randomly selects two end points from the end point group as an end point candidate. The partial structure candidate detecting section 44e further randomly selects a set of two points that are different from the two points selected first as another end point candidate, and repeats processing similar to the above until all of end point combinations are selected. For the end point candidate sets obtained as described above, all of paths connecting each end point candidate set is obtained from the thinned image 51a as a path candidate $CP_k$ (k=1, . . . N).

Figure 27C:
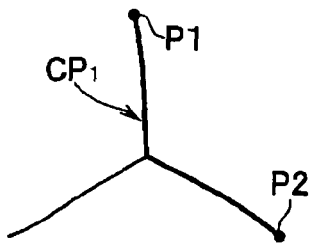
FIG. 27C is a schematic diagram for describing an example in which a living mucous membrane microstructure is divided into partial regions according to a predetermined division condition based on saliency.
Figure 27D:
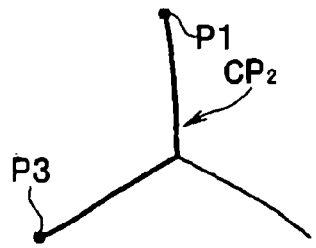
FIG. 27D is a schematic diagram for describing an example in which a living mucous membrane microstructure is divided into partial regions according to a predetermined division condition based on saliency.
Figure 27E:
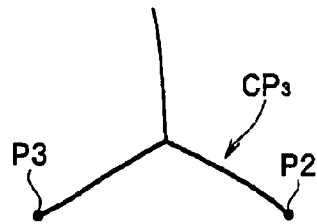
FIG. 27E is a schematic diagram for describing an example in which a living mucous membrane microstructure is divided into partial regions according to a predetermined division condition based on saliency.

In the case of the end points P1, P2 and P3 in FIG. 27B, path candidates $CP_1$, $CP_2$ and $CP_3$ such as illustrated in FIGS. 27C, 27D and 27E are detected.

Furthermore, the feature value calculating section 43a in the arithmetic operation section 41b calculates a predetermined feature value of each detected path candidate $CP_k$ in step S36 in FIG. 26. For the predetermined feature value, the feature value calculating section 43a calculates, for example, a length $l(CP_k)$ of the path candidate $CP_k$ in the living mucous membrane microstructure as a feature value for region division.

The length $l(CP_k)$ of the path candidate $CP_k$ can be obtained by, for example, calculating the total number of pixels included in each path candidate $CP_k$ in the thinned image 51a.

In step S37 in FIG. 26, the division determining section 44c in the arithmetic operation section 41b divides the living mucous membrane microstructure extracted in step S33 into partial regions with a longest path from among the respective path candidates $CP_k$ calculated in step S36 as a salient path.

More specifically, in the present embodiment, a most salient path is, for example, a longest path candidate from among all path candidates, and partial regions are obtained by selecting a longest candidate path CPmax arg=max($l(CP_k)$) in the thinned image 51a and subjecting the candidate path to processing for expansion in a width direction.

Furthermore, the living mucous membrane microstructure extracted in step S33 in FIG. 26 is divided into a partial region obtained as described above and the other partial region.

Figure 27F:
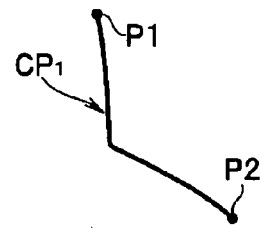
FIG. 27F is a schematic diagram for describing an example in which a living mucous membrane microstructure is divided into partial regions according to a predetermined division condition based on saliency.
Figure 27G:
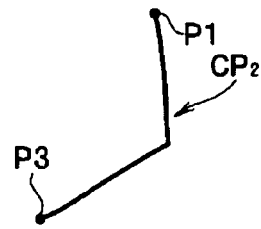
FIG. 27G is a schematic diagram for describing an example in which a living mucous membrane microstructure is divided into partial regions according to a predetermined division condition based on saliency.
Figure 27H:
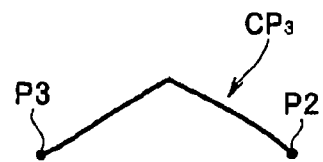
FIG. 27H is a schematic diagram for describing an example in which a living mucous membrane microstructure is divided into partial regions according to a predetermined division condition based on saliency.
Figure 27I:
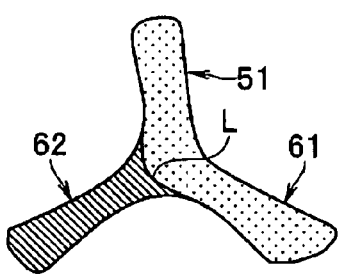
FIG. 27I is a schematic diagram for describing an example in which a living mucous membrane microstructure is divided into partial regions according to a predetermined division condition based on saliency.

In the example illustrated in FIGS. 27A to 27I, three path candidates $CP_1$, $CP_2$ and $CP_3$ illustrated in FIGS. 27C, 27D and 27E appear as illustrated in FIGS. 27F, 27G and 27H, respectively. The division determining section 44c determines that a longest candidate path CPmax in the three path candidates $CP_1$, $CP_2$ and $CP_3$ is the path candidate $CP_1$. Then, the division determining section 44c subjects the path candidate $CP_1$ to processing for expansion in the width direction, thereby generating partial regions 61 and 62 divided by a division line L as illustrated in FIG. 27I.

Figure 28:
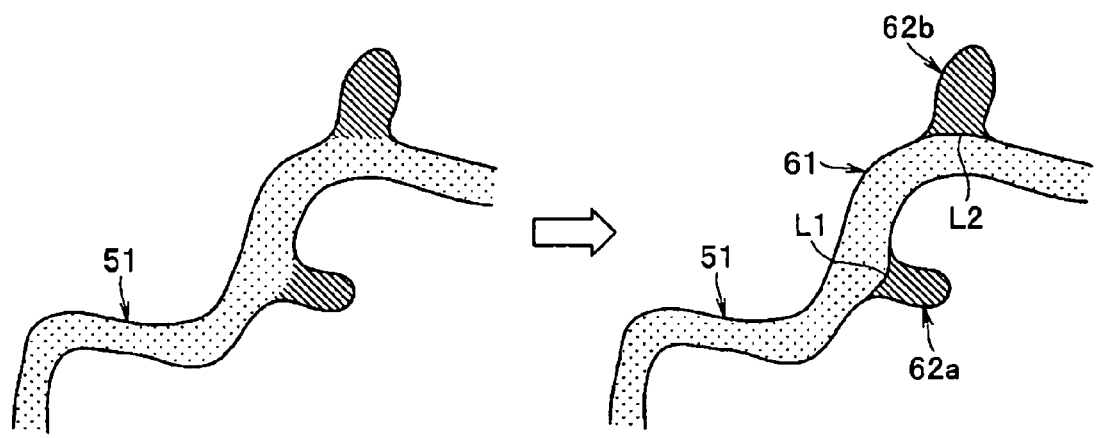
FIG. 28 is a schematic diagram illustrating an example in which a living mucous membrane microstructure is divided into partial regions according to a predetermined division condition based on length discontinuity.

Also, if a living mucous membrane microstructure 51 extracted by the extraction section 43b has a pattern shape illustrated in, for example; on the left side of FIG. 28, the arithmetic operation section 41b performs processing similar to the above, and the division determining section 44c in the arithmetic operation section 41b generates partial regions 61, 62a and 62b divided by division lines L1 and L2 on the right side of FIG. 28.

According to the present embodiment, region division processing such as described above is performed using image data generated by the image data generating section 41a, enabling a living mucous membrane microstructure appearing as a continuous pattern on the image data to be divided into partial regions in such a manner that the partial regions include a partial region having a largest length.

While the first embodiment and the second embodiment employ a region division method based on living mucous membrane microstructure discontinuity or inhomogeneity, the present embodiment can enhance the accuracy of extraction of a living mucous membrane microstructure corresponding to a finding where there is a region having a part of the living mucous membrane microstructure, the part having a salient feature value.

Also, as the processing performed by the image processing section 41 in the present embodiment, as illustrated in FIG. 29, processing according to a predetermined division condition set or selected by the division condition setting section 43d may be performed. In first step S51, a user sets or selects a predetermined division condition via the division condition setting section 43d.

After the processing in step S51, image input processing in step S52, processing for calculating feature values for extraction in step S53 and processing for extracting a living mucous membrane microstructure in step S54 are sequentially performed. Steps S52, S53 and S54 are the same processing as in steps S21, S22 and S23 in FIG. 17 (or steps S31, S32 and S33 in FIG. 26).

In step S55 after step S54, the region division section 43c determines the predetermined division condition set in step S51. Then, according to the result of the determination, the feature value calculating section 43a calculates feature values for region division.

If the first division condition is set as the predetermined division condition, in step 56, (the region division feature value calculating section 45b in) the feature value calculating section 43a calculates contrasts in a pattern of the living mucous membrane microstructure extracted in step S54 as feature values for region division.

If the second division condition is set as the predetermined division condition, in step 57, (the region division feature value calculating section 45b in) the feature value calculating section 43a calculates morphological feature values in the pattern of the living mucous membrane microstructure extracted in step S54 (more specifically, e.g., widths, lengths or running directions of the pattern) as feature values for region division.

If the third division condition is set as the predetermined division condition, in step 58, (the region division feature value calculating section 45b in) the feature value calculating section 43a calculates color tone feature values in the pattern of the living mucous membrane microstructure extracted in step S54 as feature values for region division.

If the fourth division condition is set as the predetermined division condition, in step 59, (the region division feature value calculating section 45b in) the feature value calculating section 43a calculates saliency feature values in the pattern of the living mucous membrane microstructure extracted in step S54 as feature values for region division.

In step S60 subsequent to the processing in steps S56, S57, S58 and S59, the region division section 43c divides the pattern of the living mucous membrane microstructure into partial regions according to at least any of discontinuity, inhomogeneity and non-saliency of the calculated feature values, based on the calculated feature values for region division. Then, at least any of discontinuity, inhomogeneity and non-saliency is eliminated and each of the partial regions resulting from the division exhibits a characteristic of continuity, homogeneity or saliency. The processing in FIG. 29 ends as described above.

The above-described processing enables a living mucous membrane microstructure to be divided into partial regions with good accuracy based on various feature values exhibited by a pattern of the living mucous membrane microstructure (more specifically, e.g., contrasts, color tones, widths, lengths and running directions of the pattern) so as to reflect a three-dimensional structure. Here, the processing illustrated in FIG. 29 is an example of specific processing and may be performed with a part thereof changed.

For example, two or three (thus, a plurality of) processing steps of steps S56, S57, S58 and S59 may be performed sequentially or in parallel to perform the processing in step S60 based on results of calculation of plural types of feature values. Also, for example, where morphological feature values of a pattern are calculated, for example, two types of feature values, i.e., widths and lengths of the pattern may be calculated to perform the processing in step S60 based on the result of the calculation.

Also, where feature values for region division are calculated, it is possible that a feature value calculation order setting section that sets a priority order for calculation of feature values is provided, feature values of a type with high priority are calculated in preference, and based on the result of the calculation, processing for region division is performed. It is also possible that based on the results of plural types of feature values with high priority, processing for region division may be performed. Consequently, more reliable region division and more accurate partial region extraction can be performed.

Also, the series of processing described above in the respective embodiments are not limited to ones that are applied to endoscopic images, and may be, for example, ones that are applied to images obtained from capsule endoscopes or ones that are applied to various types of medical images such as monochrome images.

Also, the series of processing described above in the respective embodiments are applied to any of a surface pattern, a pit pattern and a blood vessel in a living mucous membrane microstructure.

Also, the respective embodiments described above may be ones that perform processing using feature values calculated for respective pixels, or ones that perform processing using feature values calculated for respective small regions each including a plurality of pixels (for example, 4×4 pixels).

Also, in the above-described embodiments, for example, the second embodiment has been described as one substantially including the first embodiment; however, as mentioned as a modification of the second embodiment, may have a configuration with the first embodiment excluded. Also, the third embodiment has been described as one having a configuration substantially including the first embodiment and the second embodiment; however, as mentioned as a modification of the third embodiment, may have a configuration with the first embodiment and the second embodiment excluded.

The present invention is not limited to the respective embodiments described above, and includes embodiments resulting from partially combining the embodiments and the like including the modifications. Furthermore, it should be understood that the present invention allows various modifications and applications without departing from the spirit of the present invention.

What is claimed is:

1. An image processing apparatus comprising:
   an image input device that receives an input of an image obtained by image pickup of a living mucous membrane having a three-dimensional structure;
   an extraction device that extracts pixels corresponding to the structure appearing as a continuous pattern in the image from pixels included in the image inputted to the image input device;
   a divarication portion identifying device that identifies a divarication portion from the pixels corresponding to the structure extracted by the extraction device;
   a segment division device that divides the pixels corresponding to the structure into a plurality of segments each including the divarication portion at an end;
   a calculating device that calculates information on at least one of contrast and color tone for each of the segments divided by the segment division device from pixels corresponding to the structure extracted by the extraction device; and
   a region division device that specifies a combination of segments that provides minimum information variation in each segment calculated by the calculating device, and extracts pixels corresponding to a structure that is continuous in a three-dimensional space from the specified combination of segments.

2. An image processing apparatus comprising:
   an image input device that receives an input of an image obtained by image pickup of a living mucous membrane having a three-dimensional structure;
   an extraction device that extracts pixels corresponding to the structure appearing as a continuous pattern in the image from pixels included in the image inputted to the image input device;
   a divarication portion identifying device that identifies a divarication portion from the pixels corresponding to the structure extracted by the extraction device;
   a segment division device that divides the pixels corresponding to the structure into a plurality of segments each including the divarication portion at an end;
   a calculating device that calculates information on at least one of contrast, color tone, and width for each of the segments divided by the segment division device from pixels corresponding to the structure extracted by the extraction device; and
   a region division device that species a combination of segments that provides a maximum variation among segments of an average value or a central value or a mode value of information in each of the segments calculated by the calculating device, and extracts pixels corresponding to a structure that is continuous in a three-dimensional space from the specified combination of segments.

3. The image processing apparatus according to claim 1, wherein the segment division device specifies a combination of segments that provides a maximum variation in the information on at least one of contrast and color tone calculated by the calculating device and provides a maximum variation among segments of an average value or a central value or a mode value of the information on least one of contrast and color tone, and extracts, from the specified combination of segments, pixels corresponding to a structure that is continuous in a three-dimensional space.

* * * * *